United States Patent [19]

Shadle et al.

[11] Patent Number: 4,847,325
[45] Date of Patent: Jul. 11, 1989

[54] CONJUGATION OF POLYMER TO COLONY STIMULATING FACTOR-1

[75] Inventors: Paula J. Shadle, Richmond; Kirston E. Koths, El Cerrito; Margaret Moreland, Berkeley; Nandini Katre, El Cerrito, all of Calif.

[73] Assignee: Cetus Corporation, Emeryville, Calif.

[21] Appl. No.: 146,275

[22] Filed: Jan. 20, 1988

[51] Int. Cl.$^4$ .................. C08L 89/00; C07G 7/00; A61K 37/02
[52] U.S. Cl. .................. 525/54.1; 530/351; 514/12
[58] Field of Search .................. 530/351, 414; 435/68; 525/54.1; 514/2, 12

[56] References Cited

U.S. PATENT DOCUMENTS

| | | | |
|---|---|---|---|
| 3,619,371 | 11/1971 | Crook et al. | 195/63 R |
| 3,788,948 | 1/1974 | Kagedal et al. | 195/68 |
| 3,876,501 | 4/1975 | Hanushewsky | 195/68 |
| 3,960,830 | 6/1976 | Bayer et al. | 530/334 |
| 4,002,531 | 1/1977 | Royer | 195/68 |
| 4,055,635 | 10/1977 | Green et al. | 424/78 |
| 4,088,538 | 5/1978 | Schneider | 195/63 |
| 4,179,337 | 12/1979 | Davis et al. | 435/181 |
| 4,261,973 | 4/1981 | Lee et al. | 424/78 |
| 4,296,097 | 10/1981 | Lee et al. | 424/78 |
| 4,301,144 | 11/1981 | Iwashita et al. | 424/78 |
| 4,415,665 | 11/1983 | Mosbach et al. | 435/179 |
| 4,430,260 | 2/1984 | Lee et al. | 540/315 |
| 4,482,485 | 11/1984 | Funakoshi et al. | 530/397 |
| 4,496,689 | 1/1985 | Mitra et al. | 525/54.1 |
| 4,504,586 | 3/1985 | Nicolson | 530/397 |
| 4,609,546 | 9/1986 | Hiratani | 424/83 |
| 4,621,050 | 11/1986 | Sugimoto | 935/109 |
| 4,675,291 | 6/1987 | Yamamura et al. | 435/240.9 |
| 4,766,106 | 8/1988 | Katre et al. | 514/12 |

FOREIGN PATENT DOCUMENTS

| | | |
|---|---|---|
| 0142125 | 5/1985 | European Pat. Off. . |
| 0154316 | 9/1985 | European Pat. Off. . |
| 3340592 | 5/1985 | Fed. Rep. of Germany . |
| 86/04145 | 7/1986 | PCT Int'l Appl. . |
| 87/00056 | 1/1987 | PCT Int'l Appl. . |

OTHER PUBLICATIONS

Boccu, E. et al., 1983, *Z. Natuforsch.*, 38c:94–99.
Katre et al., 1987, *Proc. Natl. Acad. Sci.*, USA, 84:1487–1491.
Suzuki et al., 1984, *Biochem. Biophys. Acta.*, 788:248–255.
Davis et al., 1980, Biomedical Polymers, New York:Academic Press, pp. 441–451.
Abuchowski et al., 1984, *Cancer Biochem. Biophys.*, 7:175–186.
Sabet et al., *Indian J. Chem.*, Sec. A (1984), 23A(5) (Abstract only).
Wei et al., *Immunol.* (1984), 51:687–696.
Lee et al., *J. Immunol.* (1981), 126:414–418.
Hubbard et al., *J. Immunol.* (1981), 126:407–413.
Lee et al., *Int. Arch. Allergy Appl. Immunol.* (1980), 63:1–13.
Sehon, *Prog. Allergy* (1982), 32:161–202.
Holford-Strevens et al., *Int. Arch. Allergy App. Immunol.* (1982), 67:109–116.
Sehon and Lee, *Int. Arch. Allergy App. Immunol.* (1981), 66 (Supp. 1), pp. 39–42.
U.S. Application Ser. No. 53,244 by Moreland et al., filed 5/22/87:
U.S. Application Ser. No. 99,872 by Ralph et al., filed 9/22/87.
U.S. Application Ser. No. 931,197 by Aldwin et al., filed 11/14/86.

*Primary Examiner*—John Kight
*Assistant Examiner*—Nathan M. Nutter
*Attorney, Agent, or Firm*—Albert P. Halluin

[57] ABSTRACT

A biologically active CSF-1 protein is selectively conjugated via certain amino acid residues or carbohydrate moieties to a water-soluble polymer selected from polyethylene glycol or polypropylene glycol homopolymers, polyoxyethylated polyols, or polyvinyl alcohol. The resulting conjugated CSF-1 is biologically active and has increased circulating half-life in mammals, compared to that of the unconjugated protein. The conjugated CSF-1 may be used to stimulate the immune response or to provide more cells to be stimulated.

26 Claims, 10 Drawing Sheets

FIG. 1-1

```
              20                  40                    60
AGTGAGGCTC GGCCCGGGGA AAGTGAAAGT TTGCCTGGGT CCTCTCGGCG CCAGAGCCGC
              80                 100                  120
TCTCCGCATC CCAGGACAGC GGTGCGGCCC TCGGCCGGGG CGCCCACTCC GCAGCAGCCA
                                             ▲
             140                 160                  180
GCGAGCGAGC GAGCGAGCGA GGGCGGCCGA CGCGCCCGGC CGGGACCCAG CTGCCCGT ATG
                                                               Mot
                                                               -32
              200                            220
ACC GCG CCG GGC GCC GCC GGG CGC TGC CCT CCC ACG ACA TGG CTG GGC
Thr Ala Pro Gly Ala Ala Gly Arg Cys Pro Pro Thr Thr Trp Leu Gly 240              260                     280
TCC CTG CTG TTG TTG GTC TGT CTC CTG GCG AGC AGG AGT ATC ACC GAG GAG
Ser Leu Leu Leu Leu Val Cys Leu Leu Ala Ser Arg Ser Ile Thr Glu Glu
                                                       1 ─────

300                       320
GTG TCG GAG TAC TGT AGC CAC ATG ATT GGG AGT GGA CAC CTG CAG TCT
Val Ser Glu Tyr Cys Ser His Met Ile Gly Ser Gly His Leu Gln Ser 340                       360                    380
CTG CAG CGG CTG ATT GAC AGT CAG ATG GAG ACC TCG TGC CAA ATT ACA TTT GAG
Leu Gln Arg Leu Ile Asp Ser Gln Met Glu Thr Ser Cys Gln Ile Thr Phe Glu
    20   INTRON ▲ SEQUENCE 400                          420
TTT GTA GAC CAG GAA CAG TTG AAA GAT CCA GTG TGC TAC CTT AAG
Phe Val Asp Gln Glu Gln Leu Lys Asp Pro Val Cys Tyr Leu Lys
              40
              440                 460                 480
AAG GCA TTT CTC CTG GTA CAA TAC ATA ATG GAG GAC ACC ATG CGC TTC AGA GAT
Lys Ala Phe Leu Leu Val Gln Tyr Ile Met Glu Asp Thr Met Arg Phe Arg Asp
                                * 60
              500                       520
AAC ACC CCC AAT GCC ATC GCC ATT GTG CAG CTG CAG GAA CTC TCT
Asn Thr Pro Asn Ala Ile Ala Ile Val Gln Leu Gln Glu Leu Ser
                                                       80
              540                       560
TTG AGG CTG AAG AGC TGC TTC ACC AAG GAT TAT GAA GAG CAT GAC AAG GCC
Leu Arg Leu Lys Ser Cys Phe Thr Lys Asp Tyr Glu Glu His Asp Lys Ala
                                                              100
    580                 600                     620
TGC GTC CGA ACT TTC TAT GAG ACA CCT CTC CAG TTG CTG GAG AAG GTC
Cys Val Arg Thr Phe Tyr Glu Thr Pro Leu Gln Leu Leu Glu Lys Val 640                          660
AAG AAT GTC TTT AAT GAA ACA AAG AAT CTC CTT GAC AAG GAC TGG AAT ATT
Lys Asn Val Phe Asn Glu Thr Lys Asn Leu Leu Asp Lys Asp Trp Asn Ile
              120           ─────

680                        700                720
TTC AGC AAG AAC TGC AAC AAC AGC TTT GCT GAA TGC TCC AGC CAA GGC
Phe Ser Lys Asn Cys Asn Asn Ser Phe Ala Glu Cys Ser Ser Gln Gly
                    ────────────
                        140
              740                          760
CAT GAG AGG CAG TCC GAG GGA TCC TCC AGC CCG CAG CTC CAG GAG TCT GTC
His Glu Arg Gln Ser Glu Gly Ser Ser Ser Pro Gln Leu Gln Glu Ser Val
                                     160
```

FIG. 1-2

```
       780                    800                      820
TTC CAC CTG CTG GTG CCC AGT GTC ATC CTG GTC TTG CTG GCC GTC GGA
Phe His Leu Leu Val Pro Ser Val Ile Leu Val Leu Leu Ala Val Gly
                                                     180
              840                      860
GGC CTC TTG TTC TAC AGG TGG AGG CGG CGG AGC CAT CAA GAG CCT CAG AGA
Gly Leu Leu Phe Tyr Arg Trp Arg Arg Arg Ser His Gln Glu Pro Gln Arg
                                                             200
       880                      900                   920
GCG GAT TCT CCC TTG GAG CAA CCA GAG GGC AGC CCC CTG ACT CAG GAT
Ala Asp Ser Pro Leu Glu Gln Pro Glu Gly Ser Pro Leu Thr Gln Asp
                940                    960                   980
GAC AGA CAG GTG GAA CTG CCA GTG TAG AGGGAATTCTA AGACCCCTCA CCATCCTGGA
Asp Arg Gln Val Glu Leu Pro Val
                220
                  1000                   1020
CACACTCGTT TGTCAATGTC CCTCTGAAAA TGTGACGCCC AGCCCCGGAC 1040         1060          1080                  1100
ACAGTACTCC AGATGTTGTC TGACCAGCTC AGAGAGAGTA CAGTGGGACT GTTACCTTCC TTGATATGGA
            1120         1140
CAGTATTCTT CTATTTGTGC AGATTAAGAT TGCATTAGTT TTTTTCTTAA
       1160         1180          1200                  1220
CAACTGCATC ATACTGTTGT CATATGTTGA GCCTGTGGTC TATTAAAACC CCTAGTTCCA TTTCCCATAA
            1240         1260
ACTTCTGTCA AGCCAGACCA TCTCTACCCT GTACTTGGAC AACTTAACTT
       1280         1300          1320                  1340
TTTTAACCAA AGTGCAGTTT ATGTTCACCT TTGTTAAAGC CACCTTGTGG TTTCTGCCCA TCACCTGAAC
            1360         1380
CTACTGAAGT TGTGTGAAAT CCTAATTCTG TCATCTCCGT AGCCCTCCCA
       1400         1420          1440                  1460
GTTGTGCCTC CTGCACATTG ATGAGTGCCT GCTGTTGTCT TTGCCCATGT TGTTGATGTA GCTGTGACCC
            1480         1500
TATTGTTCCT CACCCCTGCC CCCCGCCAAC CCCAGCTGGC CCACCTCTTC
       1520         1540          1560                  1580
CCCCTCCCAC CCAAGCCCAC AGCCAGCCCA TCAGGAAGCC TTCCTGGCTT CTCCACAACC TTCTGACTGC
            1600         1620
TCTTTTCAGT CATGCCCCTC CTGCTCTTTT GTATTTGGCT AATAGTATAT

1640
CAATTTGCAC TT
```

FIG. 2-1

```
              CCCTGCTGTTGTTGGTCTGTCTCCTGGCGAGCAGGAGTATCACC   44
          -14 LeuLeuLeuLeuValCysLeuLeuAlaSerArgSerIleThr

GAGGAGGTGTCGGAGTACTGTAGCCACATGATTGGGAGTGGACACCTGCAGTCTCTGCAG  104
    1 GluGluValSerGluTyrCysSerHisMETIleGlySerGlyHisLeuGlnSerLeuGln

CGGCTGATTGACAGTCAGATGGAGACCTCGTGCCAAATTACATTTGAGTTTGTAGACCAG  164
   21 ArgLeuIleAspSerGlnMETGluThrSerCysGlnIleThrPheGluPheValAspGln

GAACAGTTGAAAGATCCAGTGTGCTACCTTAAGAAGGCATTTCTCCTGGTACAAGACATA  224
   41 GluGlnLeuLysAspProValCysTyrLeuLysLysAlaPheLeuLeuValGlnAspIle

ATGGAGGACACCATGCGCTTCAGAGATAACACCCCCAATGCCATCGCCATTGTGCAGCTG  284
   61 METGluAspThrMETArgPheArgAspAsnThrProAsnAlaIleAlaIleValGlnLeu

CAGGAACTCTCTTTGAGGCTGAAGAGCTGCTTCACCAAGGATTATGAAGAGCATGACAAG  344
   81 GlnGluLeuSerLeuArgLeuLysSerCysPheThrLysAspTyrGluGluHisAspLys

GCCTGCGTCCGAACTTTCTATGAGACACCTCTCCAGTTGCTGGAGAAGGTCAAGAATGTC  404
  101 AlaCysValArgThrPheTyrGluThrProLeuGlnLeuLeuGluLysValLysAsnVal

TTTAATGAAACAAAGAATCTCCTTGACAAGGACTGGAATATTTTCAGCAAGAACTGCAAC  464
  121 PheAsnGluThrLysAsnLeuLeuAspLysAspTrpAsnIlePheSerLysAsnCysAsn

AACAGCTTTGCTGAATGCTCCAGCCAAGATGTGGTGACCAAGCCTGATTGCAACTGCCTG  524
  141 AsnSerPheAlaGluCysSerSerGlnAspValValThrLysProAspCysAsnCysLeu

TACCCCAAAGCCATCCCTAGCAGTGACCCGGCCTCTGTCTCCCCTCATCAGCCCCTCGCC  584
  161 TyrProLysAlaIleProSerSerAspProAlaSerValSerProHisGlnProLeuAla

CCCTCCATGGCCCCTGTGGCTGGCTTGACCTGGGAGGACTCTGAGGGAACTGAGGGCAGC  644
  181 ProSerMETAlaProValAlaGlyLeuThrTrpGluAspSerGluGlyThrGluGlySer

TCCCTCTTGCCTGGTGAGCAGCCCCTGCACACAGTGGATCCAGGCAGTGCCAAGCAGCGG  704
  201 SerLeuLeuProGlyGluGlnProLeuHisThrValAspProGlySerAlaLysGlnArg

CCACCCAGGAGCACCTGCCAGAGCTTTGAGCCGCCAGAGACCCCAGTTGTCAAGGACAGC  764
  221 ProProArgSerThrCysGlnSerPheGluProProGluThrProValValLysAspSer

ACCATCGGTGGCTCACCACAGCCTCGCCCCTCTGTCGGGGCCTTCAACCCCGGGATGGAG  824
  241 ThrIleGlyGlySerProGlnProArgProSerValGlyAlaPheAsnProGlyMETGlu

GATATTCTTGACTCTGCAATGGGCACTAATTGGGTCCCAGAAGAAGCCTCTGGAGAGGCC  884
  261 AspIleLeuAspSerAlaMETGlyThrAsnTrpValProGluGluAlaSerGlyGluAla

AGTGAGATTCCCGTACCCCAAGGGACAGAGCTTTCCCCCTCCAGGCCAGGAGGGGGCAGC  944
  281 SerGluIleProValProGlnGlyThrGluLeuSerProSerArgProGlyGlyGlySer

ATGCAGACAGAGCCCGCCAGACCCAGCAACTTCCTCTCAGCATCTTCTCCACTCCCTGCA 1004
  301 METGlnThrGluProAlaArgProSerAsnPheLeuSerAlaSerSerProLeuProAla

TCAGCAAAGGGCCAACAGCCGGCAGATGTAACTGGTACAGCCTTGCCCAGGGTGGGCCCC 1064
  321 SerAlaLysGlyGlnGlnProAlaAspValThrGlyThrAlaLeuProArgValGlyPro

GTGAGGCCCACTGGCCAGGACTGGAATCACACCCCCCAGAAGACAGACCATCCATCTGCC 1124
  341 ValArgProThrGlyGlnAspTrpAsnHisThrProGlnLysThrAspHisProSerAla

CTGCTCAGAGACCCCCCGGAGCCAGGCTCTCCCAGGATCTCATCACTGCGCCCCCAGGGC 1184
  361 LeuLeuArgAspProProGluProGlySerProArgIleSerSerLeuArgProGlnGly
```

```
                CTCAGCAACCCCTCCACCCTCTCTGCTCAGCCACAGCTTTCCAGAAGCCACTCCTCGGGC  1244
381  LeuSerAsnProSerThrLeuSerAlaGlnProGlnLeuSerArgSerHisSerSerGly

AGCGTGCTGCCCCTTGGGGAGCTGGAGGGCAGGAGGAGCACCAGGGATCGGAGGAGCCCC  1304
401  SerValLeuProLeuGlyGluLeuGluGlyArgArgSerThrArgAspArgArgSerPro

GCAGAGCCAGAAGGAGGACCAGCAAGTGAAGGGGCAGCCAGGCCCCTGCCCCGTTTTAAC  1364
421  AlaGluProGluGlyGlyProAlaSerGluGlyAlaAlaArgProLeuProArgPheAsn

TCCGTTCCTTTGACTGACACAGGCCATGAGAGGCAGTCCGAGGGATCCTCCAGCCCGCAG  1424
441  SerValProLeuThrAspThrGlyHisGluArgGlnSerGluGlySerSerSerProGln

CTCCAGGAGTCTGTCTTCCACCTGCTGGTGCCCAGTGTCATCCTGGTCTTGCTGGCCGTC  1484
461  LeuGlnGluSerValPheHisLeuLeuValProSerValIleLeuValLeuLeuAlaVal

GGAGGCCTCTTGTTCTACAGGTGGAGGCGGCGGAGCCATCAAGAGCCTCAGAGAGCGGAT  1544
481  GlyGlyLeuLeuPheTyrArgTrpArgArgArgSerHisGlnGluProGlnArgAlaAsp

TCTCCCTTGGAGCAACCAGAGGGCAGCCCCCTGACTCAGGATGACAGACAGGTGGAACTG  1604
501  SerProLeuGluGlnProGluGlySerProLeuThrGlnAspAspArgGlnValGluLeu

CCAGTGTAGAGGGAATTCTAAGACCCCTCACCATCCTGGACACACTCGTTTGTCAATGTC  1664
521  ProVal...

CCTCTGAAAATGTGACGCCCAGCCCCGGACACAGTACTCCAGATGTTGTCTGACCAGCTC  1724
                AGAGAGAGTACAGTGGGACTGTTACCTTCCTTGATATGGACAGTATTCTTCTATTTGTGC  1784
                AGATTAAGATTGCATTAGTTTTTTTCTTAACAACTGCATCATACTGTTGTCATATGTTGA  1844
                GCCTGTGGTCTATTAAAACCCCTAGTTCCATTTCCCATAAACTTCTGTCAAGCCAGACCA  1904
                TCTCTACCCTGTACTTGGACAACTTAACTTTTTTAACCAAAGTGCAGTTTATGTTCACCT  1964
                TTGTTAAAGCCACCTTGTGGTTTCTGCCCATCACCTGAACCTACTGAAGTTGTGTGAAAT  2024
                CCTAATTCTGTCATCTCCGTAGCCCTCCCAGTTGTGCCTCCTGCACATTGATGAGTGCCT  2084
                GCTGTTGTCTTTGCCCATGTTGTTGATGTAGCTGTGACCCTATTGTTCCTCACCCCTGCC  2144
                CCCCGCCAACCCCAGCTGGCCCACCTCTTCCCCCTCCCACCCAAGCCCACAGCCAGCCCA  2204
                TCAGGAAGCCTTCCTGGCTTCTCCACAACCTTCTGACTGCTCTTTTCAGTCATGCCCCTC  2264
                CTGCTCTTTTGTATTTGGCTAATAGTATATCAATTTGC
```

FIG. 2-2

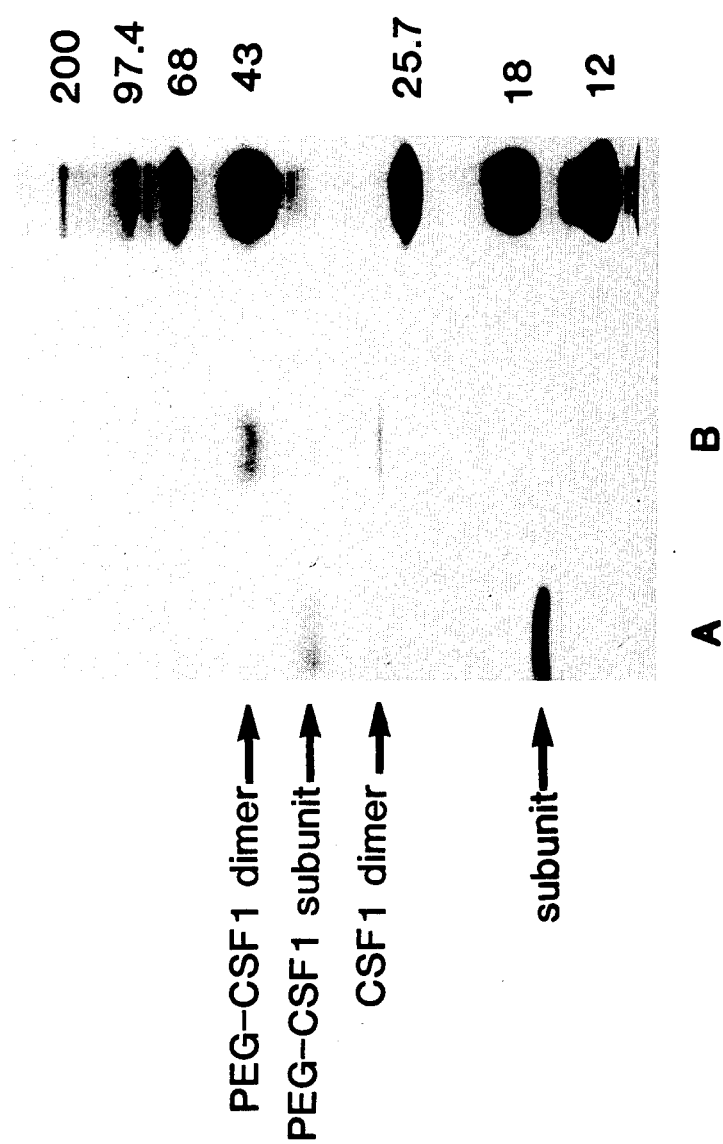
FIG. 8    SDS-PAGE analysis of 11K Peg-rCSF1 pool

CONJUGATION OF POLYMER TO COLONY STIMULATING FACTOR-1

BACKGROUND OF THE INVENTION

1. Field of the Invention

This invention relates to a chemical biologically active colony stimulating factor-1 (CSF-1) that alters the chemical and/or physiological properties of this protein. More specifically, this invention relates to selective conjugation of CSF-1 to polymers to increase the circulating half-life of the protein in mammals.

2. Background Art

Colony stimulating factor-1 (CSF-1) (also known as M-CSF) is one of several proteins that are capable of stimulating colony formation by bone marrow cells plated in semisolid culture medium. CSF-1 is distinguished from other colony stimulating factors by its ability to stimulate the formation of predominantly macrophage colonies. Other CSFs stimulate the production of colonies that consist of neutrophilic granulocytes and macrophages, exclusively neutrophilic granulocytes, or neutrophilic and eosinophilic granulocytes and macrophages. A review of these CSFs has been published by Dexter, T. M., Nature (1984) 309:746, and by Vadas, M. A., J. Immunol (1983) 130:793. There is currently no routine in vivo assay that is known to be specific for CSF-1 activity.

CSF-1 has been purified from native sources (see, e.g., copending U.S. application Ser. No. 07/002400 filed Dec. 3, 1986, assigned to the same assignee, regarding immunoaffinity chromatography of native CSF-1 to enable partial amino acid determinations). CSF-1 has also been produced from recombinant DNA using two apparently related cDNA clones: (1) a "short" form that encodes a monomeric protein of 224 amino acids preceded by a 32-amino acid signal sequence (Kawasaki, E. S., et al., Science (1985) 230:292–296); and (2) a "long" form, encoding a monomeric protein of 522 amino acids, also preceded by the 32-amino acid signal sequence. The long form has been cloned and expressed by two groups, as disclosed in copending U.S. Ser. Nos. 923,067 and 039,654, filed Oct. 24, 1986 and Apr. 16, 1987, respectively, and assigned to the same assignee and incorporated herein by reference; Wong, G., et al. Science (1987) 235:1504–1509, and PCT WO87/06954 published Nov. 19, 1987. (The DNA and amino acid sequences for these two clones are shown in FIGS. 1 and 2, respectively.) Both the long and short forms of CSF-1 are described by Clark and Kamen, Science (1987) 236:1229–1237.

The long and short forms of the CSF-1-encoding DNA appear to arise from a variable splice junction at the upstream portion of exon 6 of the genomic CSF-1-encoding DNA. When CSF-1 is expressed in certain eucaryotic cells from either the long or short cDNA forms, it is secreted as a dimeric glycoprotein and appears to be variably processed at the C-terminus and/or variably glycosylated. Consequently, CSF-1 proteins of varying molecular weights are found when the reduced monomeric form is subjected to Western analysis.

The amino acid sequences of the long and short forms, as predicted from the DNA sequence of the isolated clones and by their relationship to the genomic sequence, are identical in the first 149 amino acids at the N-terminus after signal peptide cleavage, and diverge thereafter as a result of the insertion in the longer clone of an additional 894 bp fragment (encoding 298 additional amino acids) before the codon encoding amino acid 150. Therefore, both the shorter and longer forms of the gene encode regions of identical sequence at the C-terminus, as well as at the N-terminus. Biologically active protein has been recovered when truncated cDNAs encoding only the first 150 or 158 amino acids of the mature short form, or the first 190 or 221 amino acids of the mature longer form, are expressed in eucaryotic cells.

Recombinant CSF-1 was expressed in E. coli by modifying a short clone cDNA originally described by Kawasaki et al., Science (1985) 230:291 to code for proteins that contained (1) the native N-terminus and a C-terminus at amino acid 150 of the mature protein, and (2) a truncation to delete the first two amino acids at the N-terminus and a C-terminus at amino acid 150 of the mature protein. These proteins were purified and refolded to form homodimers and were found to have apparent molecular weights on size-exclusion high performance liquid chromatography (HPLC) of about 43,000 and 40,000 daltons, respectively. CSF-1 proteins modified so that the C-terminus of the expressed protein is amino acid 150 or 158 and so that up to three amino acids at the N-terminus are deleted have also been prepared.

Small proteins (less than about 70 kd) often have a relatively short half-life in blood after intravenous injection. Rapid clearance of drugs from circulation often reduces their efficacy. It is often desirable to increase the half-life of a circulating polypeptide so that smaller amounts of the polypeptide or less frequent injections might be administered, while retaining the desired therapeutic effect. Modifications of the CSF-1 protein that might alter its half-life in vivo, reduce its immunogenicity, or reduce or eliminate aggregation of the protein that might occur when it is introduced in vivo would be desirable. Such modifications include the modification of proteins with substantially straight chain polymers such as polyethylene glycol (PEG), polypropylene glycol (PPG), dextran, or polyvinyl alcohol.

For example, U.S. Pat. No. 4,261,973 describes conjugation of immunogenic allergen molecules with non-immunogenic water-soluble polymers such as PEG or polyvinyl alcohol to reduce the immunogenicity of the allergen. U.S. Pat. No. 4,301,144 describes conjugation of hemoglobin to PEG, PPG, a copolymer of ethylene glycol with propylene glycol, or ethers, esters or dehydrated products of such polymers to increase the oxygen-carrying ability of the hemoglobin molecule. U.S. Pat. No. 4,609,546 discloses that conjugation of a polypeptide or glycoprotein such as a colony stimulating factor to a polyoxyethylenepolyoxypropylene copolymer may increase the duration of its physiological activity. The only proteins that have been tested in this fashion are enzymes or native interferon, which are readily water-soluble. PCT WO 86/04145 published July 17, 1986 discloses PEG modification of antibodies to decrease binding to Fc receptors. U.S. Pat. No. 4,179,337 discloses conjugation of water-soluble polypeptides such as enzymes and insulin to PEG or PPG to reduce the immunogenicity of the polypeptides while retaining a substantial proportion of their desired physiological activities. EP No. 154,316, published Sept. 11, 1985 to Takeda Chemical Industries, Ltd., discloses and claims chemically modified lymphokines such as IL-2 containing PEG bonded directly to at least one primary amino group of the lymphokine. In addition, Katre et al., Proc.

*Natl. Acad. Sci.* (1987) 84:1487 discloses modification of IL-2 with PEG.

Many other references disclose the concept of PEG derivatization of proteins such as alpha-1-proteinase inhibitor, asparaginase, uricase, superoxide dismutase, streptokinase, plasminogen activator, IgG, albumin, lipoprotein lipase, horseradish peroxidase, catalase, arginase and asparaginase, as well as peptides. Such derivatization through lysines was reported as improving half-life, decreasing immunogenicity, increasing solubility, and in general, increasing efficacy (which permitted less frequent dosing). In most cases, the proteins required multiple modifications per molecule to achieve improved performance in vivo, and the activity in vitro was significantly decreased by such modification.

Modification of IL-2, IFN-$\beta$ and immunotoxins with PEG through cysteine residues of a polypeptide is disclosed in PCT WO87/00056 published Jan. 15, 1987.

Copending U.S. patent application Ser. No. 053,244 filed May 22, 1987 discloses active ester forms of poly-(alkylene glycols) that do not contain an ester linkage between the poly(alkylene glycol) and the terminal carboxylic acid and can be reacted with proteins in a controlled and reproducible manner.

In addition to these patents and patent publications, several articles discuss the concept of using activated PEG or PPG as a modifying agent for proteins such as enzymes, IgG and albumin. For example, Inada et al., *Biochem. and Biophys. Res. Comm.*, 122, 845–850 (1984) disclose modifying water-soluble lipoprotein lipase to make it soluble in organic solvents such as benzene by using cyanuric chloride to conjugate with PEG. Takahashi et al., *Biochem. and Biophys. Res. Comm.*, 121:261–265 (1984) disclose modifying horseradish peroxidase using cyanuric chloride triazine with PEG to make the water-soluble enzyme active and soluble in benzene.

Patents and patent publications that disclose use of polyvinyl alcohol (PVA) in protein conjugation reactions include U.S. Pat. Nos. 4,296,097 and 4,430,260, relating to conjugation of benzylpenicillin and PVA, U.S. Pat. No. 4,496,689 (EP No. 147,761), relating to conjugation of alpha-1-proteinase inhibitor with a polymer such as heparin, PVA or PEG, EP No. 142,125 published May 22, 1985, disclosing non-covalent bonding of hemoglobin to PVA as a carrier, DE No. 2312615 (Exploaterings AB TBF), relating to crosslinked, water-insoluble PVA coupled to a protein, and DE No. 3,340,592 published May 23, 1985, relating to conjugates of PVA with human hemoglobin A.

Articles relating to conjugates of proteins and PVA include Sabet et al., *Indian J. Chem.*, Sec. A (1984) 23A(5) (disclosing PVA and protein interaction), Wei et al., *Immunol.* (1984) 51(4):687–696 (disclosing trimellityl conjugated with PVA), Lee et al., *J. Immunol.* (1981) 126:414–418 and Hubbard et al., *J. Immunol.* (1981) 126:407–413 (both disclosing DNP conjugated to PVA), Lee et al., *Int. Arch. Allergy Appl. Immunol.* (1980) 63:1–13 (disclosing antibenzylpenicilloyl IgE conjugated to PVA), Sehon, *Prog. Allergy* (1982) 32:161–202 (disclosing an allergen and hapten conjugated via PVA), Holford-Strevens et al., *Int. Arch. Allergy App. Immunol.* (1982) 67:109–116 (disclosing conjugation of PVA and an antigen/hapten), and Sehon and Lee, *Int. Arch. Allergy App. Immunol.* (1981) 66 (Supp. 1), pp. 39–42 (disclosing a hapten/allergen conjugated to PVA).

Copending U.S. application Ser. No. 099,872 filed Sept. 22, 1987 discloses various potential uses of CSF-1, including use as an anti-infection, anti-tumor, or wound-healing agent.

None of these references, however, discloses details of how to modify CSF-1 with a polymer such as PEG or polyvinyl alcohol so as to retain its biological activity while also increasing its circulating half-life or efficacy. Furthermore, it is not generally possible to predict the extent of protein modification that is desirable, because some proteins are much more susceptible to inactivation through conjugation than others.

SUMMARY OF THE INVENTION

Accordingly, the present invention provides for modifying colony stimulating factor-1 to increase its half-life in vivo, while also retaining useful biological activity. The modified CSF-1 may be used to stimulate the immune response at much reduced and/or less frequent dosage than the unmodified CSF-1.

As secondary advantages, the modification may decrease the immunogenicity of the CSF-1 (especially when used in heterologous species, such as use of human CSF-1 for cattle) and/or reduce aggregation of the protein that might occur.

More specifically, the present invention is directed to a biologically active composition having prolonged in vivo half-life in mammals, comprising a protein that stimulates the formation of primarily macrophage colonies in the in vitro colony stimulating factor-1 assay, which protein is covalently conjugated to a water-soluble polymer selected from the group consisting of polyethylene glycol or polypropylene glycol homopolymers, polyoxyethylated polyols, and polyvinyl alcohol, wherein said homopolymer is unsubstituted or substituted at one end with an alkyl group. The CSF-1 protein may be conjugated to the polymer via: (1) free amino groups, including lysine residues and the N-terminal amino acid (preferably 1 or 2 sites), (2) carbohydrate moiety(ies) of eukaryote-expressed, glycosylated CSF-1; or (3) free sulfhydryl groups engineered into the CSF-1 clone or generated by the production of heterodimers, including, but not limited to, different portions of the mature, native CSF-1 sequence.

Preferably the polymer is unsubstituted polyethylene glycol (PEG), monomethyl PEG (mPEG), or polyoxyethylated glycerol (POG) that is coupled to the (1) lysine residue(s) of the CSF-1 via an amide linkage formed from an active ester (preferably the N-hydroxysuccinimide or paranitrophenyl ester) of a PEG, mPEG, or POG carboxylic acid; (2) carbohydrate moiety(ies) of the CSF-1 via an amine, hydrazine, or hydrazide linkage; or (3) cysteine residue(s) of the CSF-1 via a maleimido or halacetyl (where halo is Br, Cl, I or F) group.

Another aspect of this invention resides in a process for preparing the conjugated protein described above, comprising:

(a) providing a water-soluble polymer having at least one terminal reactive group where the polymer is selected from the group consisting of polyethylene or polypropylene glycol homopolymers and polyoxyethylated polyols, and polyvinyl alcohol, wherein said homopolymer is unsubstituted or substituted at one end with an alkyl group;

(b) reacting the protein with the reactive group of said polymer so as to render the protein water-soluble, biologically active, and selectively conjugated; and (c) purifying the conjugated protein.

In another aspect, the invention relates to a method for prophylactic or therapeutic treatment of infectious diseases in mammals and to a method for treating tumor burden in mammals comprising administering to the mammal an effective amount of a pharmaceutical preparation comprising the conjugated CSF-1 protein dissolved in a pharmaceutically acceptable aqueous carrier medium.

BRIEF DESCRIPTION OF THE DRAWINGS

FIG. 1 shows the cDNA and deduced amino acid sequence for pCSF-17 (partial amino acid leader sequence and amino acids 1-224).

FIG. 2 shows the cDNA and deduced amino acid sequence for CSF-4 (32 amino acid leader sequence and amino acids 1-522).

FIG. 8 shows SDS-PAGE analysis of rCSF-1 derivatized with PEG-11,000 (SCSF/C∇150). Gel (10%), stained for protein with Coomassie blue, is of the sample used in FIG. 5, with and without reduction of disulfide bonds.

DESCRIPTION OF THE PREFERRED EMBODIMENTS

Definitions

Figure 3A:
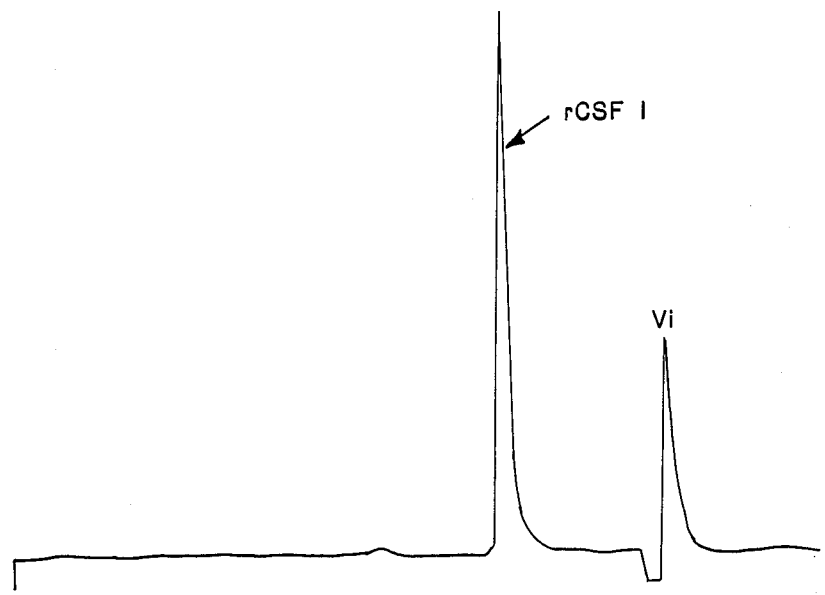
FIG. 3A shows the size exclusion HPLC chromatogram of underivatized recombinant CSF-1 (rCSF-1) (SCSF/N∇2C∇150).
Figure 3B:
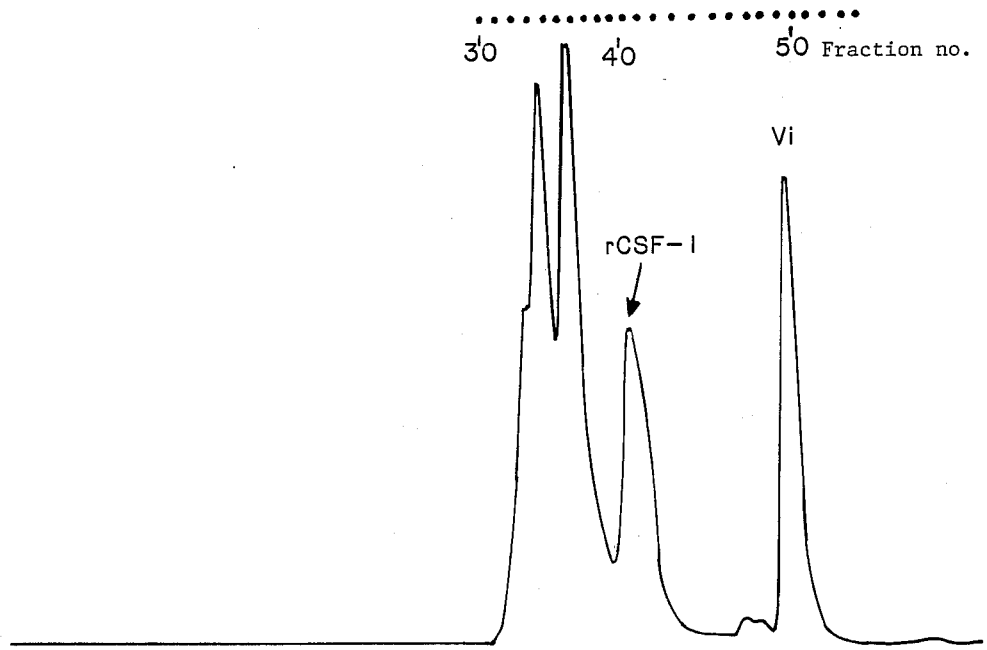
FIG. 3B shows the HPLC chromatogram of the same rCSF-1 derivatized with PEG-NHS of 7000 dalton average molecular weight.
Figure 4:
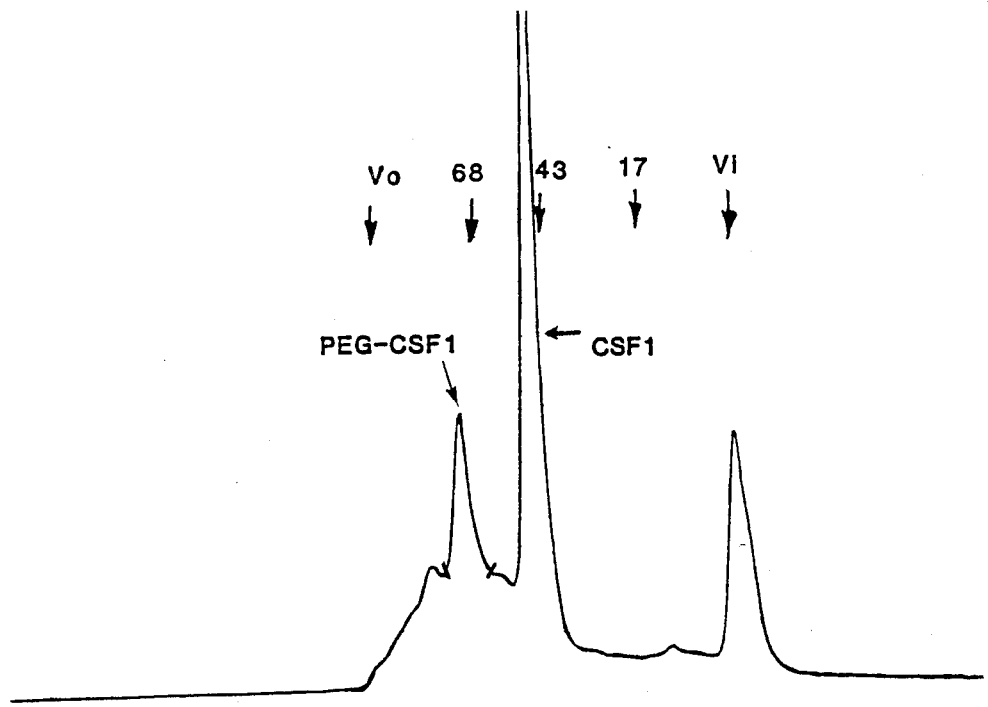
FIG. 4 shows a size exclusion HPLC chromatogram of rCSF-1 (SCSF/C∇150) derivatized with PEG-NHS of 11,000 daltons average molecular weight.

"Colony stimulating factor-1" refers to a dimeric protein or glycoprotein composition that exhibits the spectrum of biological activities understood in the art for CSF-1; i.e., when applied to the standard in vitro colony stimulating assay of Metcalf, D., *J. Cell. Physiol.* (1970) 76:89, the polypeptide stimulates the formation of primarily macrophage colonies. "Biologically active CSF-1" means a composition of conjugated CSF-1, that has essentially the same specific activity in mouse bone marrow colony-forming assays as the unconjugated form of the same CSF-1 or at least 50% of its specific activity. A "native" CSF-1 is a non-recombinant CSF-1. Murine CSF-1 is described in copending U.S. Ser. No. 876,819 filed June 20, 1986.

"Clinically pure" CSF-1 means a preparation of biologically active human CSF-1 produced recombinantly in bacteria that is at least 95% CSF-1 either by RP-HPLC or by either reducing or non-reducing SDS-PAGE analysis and has an endotoxin content of less than about 1.0 ng/mg CSF-1.

"Selectively conjugated" refers to proteins that are covalently bonded via free amino groups of the protein (preferably one or two free amino groups, to retain maximum biological activity), via free sulfhydryl groups (if any), or via a carbohydrate moiety (if any) present in the protein.

"Effective amount" and "immunotherapeutically effective amount" signify an amount effective to perform the function specified, such as to promote tumor reduction or prevent or cure infectious diseases. The exact optimal amount will depend on many factors, including the patient's clinical history, and current disease, the schedule, the route, and the response of the patient.

"Therapeutic treatment" indicates treating after the disease is contracted, whereas "prophylactic" treatment indicates treating to prevent contraction of the disease.

"Mammals" indicates any mammalian species, and includes rabbits, mice, dogs, cats, cattle, sheep, primates, and humans, preferably humans.

"Muteins" are genetically engineered proteins expressed from a nucleic acid sequence that has been altered using techniques such as site-specific mutagenesis. Such genetic alterations are designed to result in one or more substitutions, additions, and/or deletions to the amino acid sequence of the parent protein.

"Pharmaceutically acceptable" refers to a carrier medium that does not interfere with the effectiveness of the biological activity of the active ingredient(s), is stable, and is not toxic to the host to whom it is administered.

"Homodimer" refers to a dimeric protein essentially identical in its two subunits except that it also includes dimeric proteins with minor microheterogeneities that occasionally arise on processing of recombinant proteins.

CSF-1 Proteins

As set forth in the background section, CSF-1 is biologically active in its dimeric form. The CSF-1 employed herein may be the native dimer or recombinantly produced dimer. Native dimeric CSF-1 species have been obtained from human urine, cultured monocytes, and culture supernatants of some cell lines. It has been possible to obtain recombinant DNA encoding CSF-1 monomers consisting of a variety of amino acid sequences and lengths. FIGS. 1 and 2 show the DNA sequences and amino acid sequences predicted from the DNA sequences for, respectively, the full-length, unprocessed short and long forms, both of which contain a 32-amino acid signal sequence at their N-termini. The sequences of the monomeric CSF-1 protein are considered herein for convenience to be the 224-amino-acid short form without the leader sequence (designated herein as SCSF), and the 522-amino-acid long form without the leader sequence (designated herein as LCSF). Other CSF-1 dimers produced from DNA sequences modified by point mutation(s), insertion(s), deletion(s), and/or translocation(s) are also expected to benefit from the chemical modification of this invention if they are biologically active.

The recombinant CSF-1, produced in any host, whether eukayotic or prokayotic, may be conjugated to polymers via selected amino acid side groups, preferably free amino groups. Preferably, the DNA encoding CSF-1 is expressed in bacteria and the resulting CSF-1 is a homodimer after purification and refolding. If the conjugation is via a carbohydrate moiety, the host may be eukaryotic, or glycosylation may be carried out in vitro.

For convenience, the primary structure of the protein subunits encoded by the various cDNA constructs described will be designated herein using a shorthand notation, as follows: LCSF denotes the 522-amino acid sequence disclosed for the clone CSF-4, set forth in copending U.S. Ser. No. 923,067 filed Oct. 24, 1986, referred to above and shown in FIG. 2, without the signal sequence. SCSF denotes the 224-amino acid sequence disclosed for the clone pCSF-17, shown in FIG. 1, without the signal sequence, described in the Kawasaki article referred to above, *Science* (1985) 230:292–296, also incorporated herein by reference.

It will be noted that one particular pCSF-17 clone derivative has an aspartic acid residue at position 59. The disclosed LCSF clone also encodes Asp at position 59. Muteins corresponding to amino acid substitutions within the sequences depicted in FIGS. 1 and 2 are correspondingly designated by the substitution subscripted with the position. Mutein forms of CSF-1 are disclosed in copending U.S. Ser. Nos. 039,654 and 039,657, both filed on Apr. 16, 1987, the disclosures of which are incorporated herein by reference. When constructs encoding these proteins are expressed in bacteria, the final products may also retain N-terminal methionine to varying degrees. Since the extent of N-terminal methionine removal cannot be reliably predicted, this possibility is not included in the notation.

C-terminal and N-terminal truncations of these basic SCSF and LCSF sequences will be designated as C∇ or N∇, respectively. The C-terminal deletions will be followed by the number representing the number of amino acids of the native structure remaining; for the N-terminal deletions, N∇ will be followed by the number of amino acids deleted from the N-terminus. Thus, for example, LCSF/C∇150 denotes a construct encoding a protein that contains the first 150 amino acid residues of the long CSF sequence; SCSF/C∇158 denotes a construct encoding a protein that contains the first 158 amino acid residues of the short form; SCSF/N∇2 denotes a construct encoding the short form with two N-terminal amino acids deleted. (As set forth above, the LCSF and SCSF diverge beginning at position 150 and reconverge after 298 amino acids in the LCSF clone.) LCSF/N∇2C∇150 denotes a form that is the same as LCSF/C∇150, except that the two N-terminal glutamic acid residues are deleted.

Plasmids encoding a variety of CSF-1 forms are currently available, and can be expressed in bacterial systems. A form of plasmid encoding the long form of CSF-1 can be expressed in eukaryotic cells, in which case, the eukaryotic cell "processes" the clone, secreting a protein that is C-terminally truncated and has the leader sequence removed from the N-terminus. Alternatively, the clone can be truncated to express specific C-terminally deleted forms in eukaryotic or prokaryotic cells. In addition, the first two or three N-terminal codons can be deleted so that the resulting protein expressed in *E. coli* is more homogeneous. Specifically, the N-terminal methionine encoded just upstream of the mature native sequence N-terminus in the *E. coli* constructs (which is retained in the protein as "N-terminal met" unless removed by post-translational processing) is more readily removed from these N-terminal deletion constructs. Furthermore, significant heterogeneity detectable using reverse-phase HPLC (RPHPLC) is found when the gene encoding the "native" N-terminal sequence (for example, of the short form, mutein SCSF/C∇150) is expressed in *E. coli* and the purified product is characterized. This heterogeneity is eliminated when the corresponding CSF-1 gene lacking the two N-terminal codons (glutamic acid) is expressed. Correspondingly, N-terminal truncated forms of other short and long CSF-1 gene constructs can also be employed.

Preferred constructions are those wherein the protein consists essentially of an amino acid sequence selected from the group consisting of LCSF/C∇150 through C∇464, tyr$_{59}$LCSF/C∇150 through C∇464; SCSF/C∇150 through C∇166; and the gln$_{52}$ muteins thereof. More preferred are those CSF-1 proteins consisting essentially of an amino acid sequence selected from the group consisting of LCSF/C∇150;

| | | | |
|---|---|---|---|
| tyr$_{59}$LCSF/C∇150; | LCSF/C∇190; | tyr$_{59}$LCSF/C∇190; | LCSF/C∇221; |
| tyr$_{59}$LCSF/C∇221; | LCSF/C∇223; | tyr$_{59}$LCSF/C∇223; | LCSF/C∇236; |
| tyr$_{59}$LCSF/C∇236; | LCSF/C∇238; | tyr$_{59}$LCSF/C∇238; | LCSF/C∇249; |
| tyr$_{59}$LCSF/C∇249; | LCSF/C∇258; | tyr$_{59}$LCSF/C∇258; | LCSF/C∇411; |
| tyr$_{59}$LCSFC∇411; LCSF/C∇464; tyr$_{59}$LCSF/C∇464; SCSF/C∇150; SCSF/C∇153; | | | |
| SCSF/C∇158; and the gln$_{52}$ muteins thereof. | | | |

Particular preferred constructions that result in CSF-1 proteins for modification herein include clones encoding LCSF/C∇190, LCSF/C∇221, and their corresponding N∇2 and N∇3 and tyr$_{59}$ forms, SCSF/C∇158, and SCSF/C∇150.

The most preferred starting materials are the products of the clones encoding SCSF/C∇150; SCSF/N∇3C∇150; SCSF/N∇2C∇150; and SCSF/N∇3C∇158.

Alternatively, the CSF-1 may be in the form of a heterodimer prepared from among various monomeric units of CSF-1, particularly if the conjugation is done through a reactive cysteine residue of the CSF-1 heterodimer. The large number of CSF-1 proteins formed by variations in C-terminal processing provides a variety of starting materials that can be utilized in heterodimer formation. Thus, novel heterodimeric materials can be formed by refolding. For example, the monomeric form of SCSF/C∇150, along with the monomeric form of LCSF/C∇157, can be mixed and treated according to the method of copending U.S. application Ser. No. 114,001 filed Oct. 27, 1987, the disclosure of which is incorporated herein by reference. The heterodimer can then be separated from the homodimeric and oligomeric side products by various chromatographic methods. The heterodimer (particularly SCSF/C∇150 and LCSF/C∇157) can be made to terminate on one subunit at the 157 position, providing a potentially free sulfhydryl group for reaction with the conjugation polymer.

Similar mixtures subjected to the method of the invention could lead to heterodimers of components having amino acid substitutions—e.g., glu$_{52}$ LCSF/C∇221 and LCSF/C∇190.

The differing monomers may be mixed in vitro or produced in the same cell. If produced in the same cell, a construct for expression of each monomer is introduced into the same host; in such embodiments, it is preferred that each construct bear a different marker (such as tetracycline resistance (Tc ®) and Ampicillin resistance (Amp ®), so that cotransformed hosts are selected. The cotransformed cells are then grown and induced to obtain mixtures of the two forms.

In addition, single cysteine residues can be engineered into CSF-1 in a non-natural location to create a construct of rCSF-1 containing a free sulfhydryl group on a cysteine residue for PEG reaction, provided the molecule retains bioactivity. Also, carbohydrate moieties can be placed on the CSF-1 protein, either by expression from eukaryotic systems or by in vitro glycosylation with enzymes.

Recombinant CSF-1 proteins may or may not retain the exact length prescribed by the clone, due to processing by the host. Therefore, although the starting material proteins are referred to by the same designation, it should be understood that these designations, in reality, refer to the clone construct, and the actual length of the starting material for the process disclosed herein may be shorter, or longer (if it has N-terminal Met), than that specified by the C-terminal amino acid number.

As mentioned above, the CSF-1 may be produced in eukaryotic cells, e.g., mammalian, insect, or yeast cells. Production in mammalian cells is described in copending U.S. application Ser. No. 876,819 filed June 20, 1986. The CSF-1 may be produced from insect cells using a baculovirus vector, as described in copending U.S. Ser. No. 077,188 filed July 24, 1987, the disclosure of which is incorporated herein by reference. Other descriptions of this type of CSF-1 production are contained within Weaver et al., *Bio/Technology* (1988)6:287. Insect-cell-produced CSF-1 (SCSF/C∇150) is a glycosylated dimer that was found to have a very short in vivo half-life. The two N-linked glycosylation signals in the amino acid sequence of SCSF (Asn 122 and Asn 140) could be modified in the DNA using site-directed mutagenesis to generate a non-glycosylated, bioactive insect-cell-produced CSF-1 protein (Gln 122, Gln 140). This protein can then be reacted via its lysine or cysteine residues with a polymer as done with prokaryote-expressed rCSF-1 to increase its in vivo half-life.

The polymer can be attached covalently to the glycosylated CSF-1 on the carbohydrate, by reacting, for example, PEG-amine, PEG-hydrazine, or PEG-hydrazide with CSF-1 protein that has been oxidized with periodate to convert vicinal diols of the sugars to aldehydes. The PEG-amine can be prepared by converting PEGOH to PEG-tosylate and then to PEG-phthalimide, and the phthalimide is cleaved with hydrazine to produce $PEG-NH_2$ in a Gabriel synthesis. PEG-hydrazine and PEG-hydrazide can be prepared by methods known to those skilled in the art. The PEG derivative will couple at carbohydrate sites where vicinal diols were converted to aldehydes.

If CSF-1 is produced intracellularly in bacterial hosts, it must be refolded to form active dimers, as described in copending U.S. patent application Ser. No. 114,001 filed Oct. 27, 1987, the disclosure of which is incorporated herein by reference. Briefly, in this procedure the solubilized monomer, whether secreted or produced as a mature or fusion protein, is maintained in a chaotropic environment under reducing conditions. Such maintenance involves the use of a suitable reducing agent such as β-mercaptoethanol or dithiothreitol (DTT). The solubilized protein is typically maintained in, for example, 8M urea or 7M guanidinium hydrochloride, at a pH of about 7–8.6, in the presence of about 2–100 mM thiol compound. Starting with this solubilized form, the monomer may either be refolded directly or purified from remaining proteins by a suitable purification procedure such as chromatography on an adsorbant gel, chromatography using an ion exchange column, or gel-permeation chromatography prior to refolding. Gel-permeation chromatography is useful, as it permits an easy size separation of the desired monomer length, which is generally known in advance, from impurities of differing molecular weights. DEAE Sepharose chromatography in urea is even more useful, as it concentrates as well as purifies and is more easily scaled up than is sizing. It is preferable that the purification be conducted under reducing conditions to prevent the formation of disulfide-linked aggregates.

Thus, regardless of the chromatographic procedure used, a suitable reducing agent is included in the solutions used to load the chromatographic columns or batches and in the eluting solutions. In some instances, low pH may be substituted for reducing agent, as low pH will essentially prevent disulfide bond formation and is compatible with some chromatographic systems. In addition, inclusion of a low concentration of a chelating agent may help to preserve the reduced form of the protein.

The partially purified monomer is then subjected to refolding conditions for the formation of the dimer. The protein concentration during this step is of considerable importance. Generally, final percent yields per volume of the CSF-1 refolding reaction are increased if the protein concentration is less than about 2 mg/ml of the CSF-1 protein; a concentration range of 0.03–0.5 mg/ml is preferred. The refolding conditions may include gradual removal of the chaotropic environment over an appropriate time period, usually several hours, or dilution of the sample to the desired concentration of protein and chaotropic agent. Also possible are methods that provide a constant protein concentration, such as dialysis or hollow fiber diafiltration, while the chaotrope is slowly removed. At the end of the process, when the chaotrope is depleted, a relatively non-denaturing level is reached. For example, if guanidine hydrochloride is used as a chaotrope, a final concentration of less than about 2M, and preferably 0.1–1M, is attained, and if urea is used as the chaotrope, a final concentration of less than about 1M, and preferably 0.1–0.5M, is attained.

The refolding is conducted so as to permit oxidation of the sulfhydryl groups to disulfides that establish the biologically active dimeric configuration that, in the case of CSF-1, requires the formation of disulfide bonds, one or more of which links the two chains. One or more intrachain disulfides are also formed. Suitable redox conditions that encourage this formation of dimers include the sulfhydryl/disulfide reagent combinations, such as oxidized and reduced glutathione. The ratio of reduced to oxidized glutathione or other sulfhydryl/disulfide combination is typically from about 2 mM/0.1 mM to 0.5 mM/1.0 mM. Other methods of oxidation are also acceptable. In any event, the pH of the solution during the refolding process should be maintained at about 7.5 to 9.0 to favor the reaction. It is clear that during the process of refolding the highly reducing conditions under which the initial purification was conducted are no longer employed. The exclusion of significant concentrations of salts, such as sodium chloride, during the refolding process, permits the use of ion exchange chromatography as a subsequent concentration/purification step.

During the refolding process higher oligomeric species of CSF-1 may be formed. This aggregation process is minimized through temperature control, wherein low temperatures of about 0°-4° C. are preferable to higher temperatures of 25°-37° C.

Residual redox reagents present in the refolded CSF-1 preparation may possibly facilitate disulfide exchanges during subsequent purification steps. Two more preferred procedures to block such unwanted disulfide exchanges include lowering the pH to below 7.0 or diafiltration to remove the redox reagents.

For example, prior to further purification of the refolded, dimeric CSF-1, removal of the redox material and concentration of the refolded proteins may be performed by direct loading of the refolded material onto an ion exchange chromatography column using, for example, DEAE Sepharose. Frequently such procedures are carried out at pHs around 8; however, lowering the pH into the range of 5.5 to 7.0 reduced oligomer formation and increased yield of dimeric CSF-1.

After refolding, concentration, and purification, the dimer is further purified from residual redox material and from other proteins using procedures similar to those set forth above for the monomer. Suitable means, in particular, include gel filtration, hydrophobic interaction chromatography, ion exchange chromatography, and reverse-phase HPLC.

A particularly successful protocol for removal of undesirable impurities such as pyrogens or other endotoxins includes the use of chromatography on a phenyl-TSK or phenyl-Sepharose column. The chromatography is carried out under conditions and with reagents that are essentially endotoxin-free. The desired dimeric CSF-1 is soluble and stable in approximately 1.5M ammonium sulfate at neutral pH, and is loaded onto the columns under these conditions at low temperatures, i.e., from abut 4° C. to about 10° C., and preferably about 4° C. Removing the precipitate that forms on adding the ammonium sulfate removes some aggregates and unstable forms of refolded CSF-1. The CSF-1 protein can be eluted using a gradient of decreasing ammonium sulfate (1.5 to 0M) with increasing ethylene glycol (0 to 50%) in neutral buffer. The CSF-1 dimer elutes at approximately 0.6M ammonium sulfate, 35% ethylene glycol from the phenyl-TSK column. Propylene glycol may be used instead of ethylene glycol, in which case the elution conditions will be somewhat different. Alternative supports can also be used, and phenyl-Sepharose is, in fact, preferred for larger scale production of the purified CSF-1 dimeric protein.

Conjugation

The CSF-1 protein described above is conjugated to the polymer via either (1) free amino group(s), preferably only one or two in order to minimize loss of biological activity, (2) at least one carbohydrate moiety on the protein, or (3) free sulfhydryl group(s) that is/are engineered into the clone and remain free after refolding.

The number of polymer molecules that have been conjugated to the protein can be determined by various methods, including, for example, acid degradation or digestion, followed by amino acid analysis if the links are maleimido or bromoacetyl to cysteine links and the extent of derivatization is high (more than 4 moles/mole). Alternatively, the conjugated protein can be digested into small fragments with an enzyme (e.g., trypsin) and separated by column chromatography. A peptide map of the protein before and after modification would be compared, and fragments with altered elution times sequenced to determine the location(s) of polymer attachments. In a third alternative, the polymer can be radioactively labeled prior to coupling to determine how many moles of radioactive polymer are attached per mole of CSF-1 protein.

The residue(s) to be conjugated may be: (1) any free amino groups ($\epsilon$-amino groups at lysine residues or a free amine group, if any, at the N-terminus), (2) free sulfhydryl groups on cysteine residues that are engineered or constructed into CSF-1, or (3) carbohydrate moiety (discussed elsewhere). It has been found that if the protein is moderately derivatized on free amino groups with PEG (i.e., contains about one or two modified amino acid residues), it retains essentially the same bioactivity as underivatized CSF-1. If, however, it is highly derivatized with PEG, the conjugated protein retains about 10-15% residual bioactivity, depending on the type of CSF-1 and length of PEG polymer employed.

The polymer to which the protein is attached is a homopolymer of polyethylene glycol (PEG) or of polypropylene glycol (PPG), a polyoxyethylated polyol, or polyvinyl alcohol, provided in all cases that the polymer is soluble in water at room temperature. Examples of polyoxyethylated polyols include polyoxyethylated glycerol, olyoxyethylated sorbitol, polyoxyethylated glucose, and the like.

The glycerol backbone of polyoxyethylated glycerol is the same backbone occurring naturally in, for example, animals and humans in mono-, di- and triglycerides. Therefore, this compound might not necessarily be seen as foreign in the body.

The polymer preferably has an average molecular weight between about 1000 and 100,000 daltons, more preferably between 4000 and 40,000 daltons, depending, for example, on the molecular weight of the particular CSF-1 employed. Since the object of the modification is to obtain a conjugated protein with retained biological activity, with enhanced in vivo half-life over the unconjugated protein, and with reduced immunogenicity, the molecular weight of the polymer will be chosen to optimize these conditions, e.g., a modified dimeric CSF-1 protein of over about 80 Kd apparent molecular weight.

An additional advantage gained in derivatizing native dimeric CSF-1 (i.e., non-recombinant protein) is that the use of a scarce CSF-1 that is hard to purify would be maximized by such a modification.

Preferably the PEG homopolymer is substituted at one end with an alkyl group, but it may also be unsubstituted. Preferably the alkyl group is a $C_1$-$C_4$ alkyl group, and most preferably a methyl group. Most preferably, the polymer is a monomethyl-substituted PEG homopolymer and has a molecular weight of about 4000 to 40,000 daltons.

The covalent modification reaction may take place by any of the methods described above, preferably at about pH 5-9, more preferably 7-9 if the reactive group on the protein is a free amino group. Using the latter approach, the protein is conjugated via at least one terminal reactive group added to the polymer. The polymer with the reactive group(s) is designated herein as "activated polymer". The reactive group(s) selectively react with a free amino or other reactive group of the protein. (If there is more than one reactive group, the conjugation conditions must be carefully controlled to prevent crosslinking; however, monovalent species are preferred.) The amount of intact activated polymer employed is generally about 1- to 30-fold molar excess of the active polymer over the protein and is preferably no more than about 11 moles per mole of CSF-1 dimer for derivatization of amino groups, and most preferably is about 5 to 8 moles per mole of CSF-1.

Generally the process involves preparing an activated polymer and thereafter reacting the protein with the activated polymer. Typically, the reaction is carried out in a buffer of pH about 7-8, frequently at about 10 mM Hepes pH 7.5, 100 mM NaCl, if an internal-ester-free PEG-NHS reagent as described below is used. The reaction is carried out generally at 0° to 25° C. for from about 20 minutes to about 12 hours, preferably 25-35 minutes at 20° C. or three hours at 4° C. Following the conjugation, the desired product is recovered and purified by column chromatography or the like.

The modification reaction with active PEG can be performed in many ways, described below, using one or more steps. Examples of suitable modifying agents that can be used to produce the activated PEG in a one-step reaction include cyanuric acid chloride (2,4,6-trichloro-S-triazine) and cyanuric acid fluoride.

In one preferred embodiment the modification reaction takes place in two steps wherein the PEG-OH is reacted first with an acid anhydride such as succinic or glutaric anhydride to form a carboxylic acid, and the carboxylic acid is then reacted with a compound capable of reacting with the carboxylic acid to form an activated PEG with a reactive ester group that is capable of reacting with the protein. Examples of such compounds include N-hydroxysuccinimide, sulfo-N-hydroxysuccinimide, 4-hydroxy-3-nitrobenzene sulfonic acid, and the like. Preferably, N-hydroxysuccinimide is used.

For example, monomethyl-substituted PEG may be reacted at elevated temperatures, preferably about 100°-110° C. for four hours, with glutaric anhydride. The monomethyl PEG-glutaric acid thus produced is then reacted with N-hydroxysuccinimide in the presence of a carbodiimide reagent such as diyclohexyl or diisopropyl carbodiimide to produce the activated polymer, methoxypolyethylene glycol-N-succinimidyl glutarate, which can then be reacted with the protein after purification. This method is described in detail in Abuchowski et al., *Cancer Biochem. Biophys.*, 7:175-186 (1984).

In another example, the monomethyl-substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described in Bhatnagar et al., *Peptides: Synthesis-Structure-Function, Proceedings of the Seventh American Peptide Symposium*, Rich, et al. (eds.) (Pierce Chemical Co., Rockford Ill., 1981), p. 97-100, in Nitecki et al., *High-Technology Route to Virus Vaccines* (American Society for Microbiology: 1985), pages 43-46 (based on talk Nov. 8-10, 1984), entitled "Novel Agent for Coupling Synthetic Peptides to Carriers and Its Application", and in Aldwin et al., *Anal. Biochem.* (1987) 164:494-501. The disclosures of all of these are incorporated herein by reference.

As ester bonds are chemically and physiologically more reactive than amide bonds, it may be preferable to derivatize the protein with activated polyethylene glycol molecules that would not generate esters in the final product.

In one embodiment, the PEG may be activated for attachment to the protein using PEG-amine or PEG-OH as starting materials. The PEG-OH may be converted to the PEG-amine as described by V. N. R. Pillar et al., *J. Organic Chem.*, 45:5364-5370 (1980), the disclosure of which is incorporated herein by reference. Briefly, monomethyl PEG-amine (mPEG) is prepared by converting mPEGOH to mPEG-tosylate and then to mPEG-phthalimide, and the phthalimide is cleaved with hydrazine to produce mPEG-NH$_2$ in a Gabriel synthesis. The mPEG-amine is then reacted with glutaric anhydride at room temperature for about four hours to produce mPEG-NHCO(CH$_2$)$_3$COOH. After the reaction the product is precipitated, purified, and reacted with N-hydroxysuccinimide and dicyclohexylcarbodiimide to produce

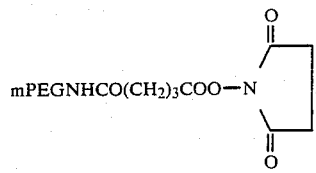

This compound can then be reacted with the appropriate free amino group(s) of the CSF-1 polypeptide.

In another embodiment, active ester forms of polyethylene glycol carboxylic acid useful for such conjugation are described in copending U.S. application Ser. No. 053,244, filed May 22, 1987, the disclosure of which is incorporated herein by reference. Briefly, the active esters have a formula of:

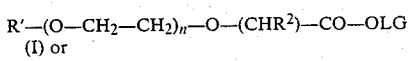
(I) or

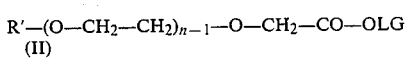
(II)

wherein R' is a lower alkyl group of 1-4 carbon atoms, R$^2$ is H or an organic substituent, n is about 8-500, LG is a leaving group selected from cyanomethyl, an aromatic group selected from a phenyl or naphthyl group substituted with from 1 to 5 substituents that render the aromatic group more labile, and a pyridyl group optionally containing 1-4 of these substituents. These esters may be produced, for Compound I, by alkylation of the polyethylene glycol with an alpha-haloalkanoic acid or ester thereof followed by esterification with HO—CH$_2$—CN or the group corresponding to LG, or, for Compound (II), by oxidation of the PEG to its acid, followed by esterification with HO—CH$_2$—CN or the group corresponding to LG. Most preferably, Formula I is prepared and the activating agent is para-nitrophenol or ortho-nitrophenol. Most preferably, the polymer is conjugated to the protein via an amide linkage formed from the para-nitrophenyl ester of the polymer.

For example, the PEG-OH may be converted to PEG—O⁻ and reacted with BrCH₂CO₂CH₃, the methyl ester may be hydrolyzed, and the acid may be reacted with p-nitrophenol in the presence of dicyclohexylcarbodiimide to produce

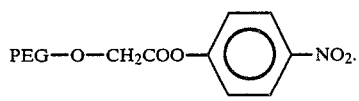

This polymer is, following purification, in turn reacted with available free amino group(s) of the CSF-1.

Homodimeric recombinant CSF-1 from *E. coli* does not contain significant numbers of reactive free sulfhydryl groups after refolding has correctly proceeded to completion. The clone could be modified genetically, however, to include one or more novel cysteine residues that might retain sulfhydryl groups following refolding. The CSF-1 mutein so produced must still retain significant biological activity to be useful herein.

Alternatively, free sulfhydryls can be generated by creation of selected heterodimers or by partial refolding of homodimers such that certain SH groups, such as on cys159, are available for modification by activated polymers.

If the protein is being conjugated via a cysteine residue, a preferred mode of conjugation is as follows: mPEG-NH₂ as described above is reacted at room temperature for preferably 0.5–1.5 hours with N-maleimido-6-aminocaproic ester of 4-hydroxy-3-nitrobenzene sulfonic acid (mal-sac-HNSA), which is described by Nitecki et al., *High-Technology Route to Virus Vaccines* (Amer. Soc. for Microbiol., 1985), pp. 43–46, mentioned supra. The latter reaction is preferably conducted with about a 5-fold molar excess of mal-sac HNSA over PEG-NHNH₂. After removal of hydrolysed or unreacted mal-sac HNSA (e.g., by dialysis, diafiltration, or size-exclusion chromatography), the reagent can then be reacted with the protein at room temperature in a buffer using equimolar amount of reagent and protein. Other reagents, such as N-succinimidyl-4-(N-maleimidomethyl)-cyclohexane-1-carboxylate (SMCC), or XCH₂CO—NH(CH₂)₅—HNSA ester wherein X is Br, Cl, or I, can perform the same function as mal-sac HNSA under a variety of reaction conditions known to those skilled in the art.

Formulations

The protein thus modified is then formulated in a non-toxic, stable, pharmaceutically acceptable aqueous carrier medium, preferably at a pH of about 3 to 8, more preferably 5–8, for administration by conventional protocols and regimens, preferably systemic, including intravenous administration. For in vitro applications, as for diagnostic purposes, the modes of administration and formulation are not critical. Aqueous formulations compatible with the culture or perfusion medium will generally be used. When used in vivo for therapy, the composition may include conventional physiologically acceptable excipients, such as water for injection, buffers, and stabilizers, as is known in the art. A water-soluble carrier such as mannitol may optionally be added to the medium. A summary of formulation techniques for pharmaceutical compositions, including protein, is found, for example, in *Remington's Pharmaceutical Sciences*, Mack Publishing Co., Easton, Pa., latest edition.

The dosage level of protein in the formulation will depend on the in vivo efficacy data obtained after preclinical testing and may vary depending upon the clinical application. The medium in which the protein is dissolved will be at a pharmaceutically acceptable pH when the mixture is reconstituted.

If the formulation is lyophilized, the lyophilized mixture may be reconstituted by injecting into the vial a conventional parenteral aqueous solvent such as, e.g., distilled water for injection.

The reconstituted formulation prepared as described above is suitable for parenteral administration to humans or other mammals in therapeutically effective amounts (i.e., amounts that eliminate or reduce the patient's pathological condition without mortality or unacceptable morbidity) to provide therapy thereto. CSF-1 therapy may be appropriate for a variety of indications such as enhancing the immune system, enhancing cytotoxicity of macrophages, increasing monocytic white blood cell count, treating infectious diseases such as cytomegalovirus and bacterial infections (e.g., Gram-negative sepsis) by therapeutic or prophylactic administration to mammals, treating tumor burden such as sarcoma or melanoma in mammals, and/or healing wounds in mammals. In addition, CSF-1 may be combined with G-CSF for stimulation of the immune system, as described in copending U.S. application Ser. No. 948,159 filed Dec. 31, 1986, the disclosure of which is incorporated herein by reference.

The dose and dosage regimen of the conjugated CSF-1 will depend, for example, upon the pharmacokinetics of the drug, the nature of the disease or condition, the type and length of polymer, the characteristics of the particular CSF-1, e.g., its therapeutic index, its spectrum of activities, the patient, and the patient's medical history. Different modified CSF-1 proteins are expected to have different pharmacokinetic and therapeutic properties that are advantageous for different routes of administration. A long-acting drug might only be administered every 3–4 days, every week, or once every two weeks. The clearance rate can be varied to give ultimate flexibility to fit the particular need of the patient by changing, e.g., the type of polymer, the size of the polymer attached, and the amino acid sequence to which the polymer is attached.

In the following examples, which illustrate the invention further, all parts and percentages are by weight unless otherwise noted, and all temperatures are in degrees Celsius.

EXAMPLE I

Preparation of PEGylated CSF-1 Via Linkage Method One

A. Preparation of Activated PEG-NHS

A linear ester of monomethyl PEG of average molecular weight 7000 can be obtained by first reacting monomethyl PEG-7000, which is available from Union Carbide, with glutaric anhydride at 100° to 110° C. for four hours or by a method similar to that of Abuchowski et al., *Cancer Biochem. Biophys.*, 7:175–186 (1984), the disclosure of which is incorporated herein by reference. The resulting PEG-glutarate was reacted with N-hydroxysuccinimide in the presence of dicyclohexylcarbodiimide, as described in detail by Abuchowski et al., supra, on page 176. The resulting product is methoxypolyethylene glycolyl N-succinimidyl glutarate, hereinafter designated as PEG*-7000. Reaction of PEG-4800 (available from Union Carbide) by the same method resulted in PEG*-4800.

A PEG-11,000 glutaramido NHS species (PEG"-11,000) was prepared as follows, according to the procedure of Rajasekharam Pillai et al., *J. Org. Chem.* 45:5364–5370 (1980): A linear monomethyl PEG of average molecular weight 11,000 daltons obtained from Union Carbide (1.5 mmole) was first dissolved in 10 ml methylene chloride and then 1.8 ml (22.2 mmole) of pyridine and 6.0 g (31.6 mmole) p-toluenesulfonyl chloride were added. The flask was flushed with nitrogen and the reaction mixture stirred at room temperature overnight. The mixture was concentrated to about 5 ml and the product precipitated with 75 ml ethyl ether. The precipitate was collected and washed with ether. The product (mPEG-tosylate) was recrystallized from ethanol.

The mPEG-tosylate (about 1.5 mmole) was dissolved in 20 ml dimethylformamide, and 2.5 g (17.0 mmole) potassium phthalimide was added. The solution was heated at reflux under nitrogen for four hours. The precipitate that formed was filtered off and the filtrate was added dropwise to 300 ml ether to precipitate the product. The product was filtered and washed with ether. The product was suspended in 30 ml methylene chloride and stirred for 0.5 hours. Insoluble impurities were filtered off and the product (mPEG-phthalimide) was precipitated with ether. Next, the mPEG-phthalimide (about 1.1 mmole) was dissolved in 15 ml ethanol and 2.0 ml (41.2 mmole) hydrazine hydrate was added. The mixture was refluxed overnight. The reaction mixture was cooled to room temperature and the product was precipitated with ether.

The precipitate was collected by filtration and resuspended in 25 ml methylene chloride. Insoluble impurities were filtered off and the product was precipitated with ether. This precipitate, mPEG-11,000-amine, was suspended in $CH_2Cl_2$, filtered, and precipitated with ether two more times. The second time it was completely soluble in methylene chloride.

A total of 0.5 g of the mPEG-11,000-amine was dissolved in 10 ml dioxane to which was added 0.25 g glutaric anhydride. The reaction was carried out for for hours at room temperature. After the reaction, the product, mPEG-NHCO$(CH_2)_3$COOH, was precipitated with about 100 ml ether. The mixture was filtered, and the product was redissolved in $CH_2Cl_2$, filtered into ether, filtered and dried. The yield of product was 200 mg.

The mPEG-NHCO$(CH_2)_3$COOH was then reacted with N-hydroxysuccinimide in the presence of dicyclohexylcarbodiimide, as described above for preparing PEG*-7000. The resulting product is designated herein as PEG"-11,000.

B. Purification and Refolding of CSF-1

An *E. coli* strain HW22, transformed with the plasmid pJN653 containing the SCSF/N∇3C∇158 gene (the plasmid being deposited as ATCC No. 67,561 on Nov. 12, 1987) was grown in a 10-liter fermenter in basal medium containing 96 mM $(NH_4)_2SO_4$, 28 mM $KH_2PO_4$, 4 mM $Na_3$ citrate.$2H_2O$, 1.7 ml/l TK9 (30 mM $ZnSO_4$, 30 mM $MgSO_4$, 1 mM $CuSO_4$), with sterile additions of 6.5 g/l glucose, 2.2 mM $MgSO_4.7H_2O$, 95 μM, $FeSO_4.7H_2O$, and 26 mg/l thiamine.HCl at 30° C. until an $OD_{680nm}$ of 10 was reached. Casamino acids were then added to 2% w/v. CSF-1 expression was induced by shifting the temperature of the culture to 37° C. After four hours the absorbance at 680 nm reached 79.

The cells were harvested by 5-fold concentration and diafiltered against ten volumes of 5 mM EDTA, pH 8.5, using Dorr-Oliver tangential cross-flow microporous filtration. The cells were disrupted by three passes at 7,500 psi in a Manton-Gaulin high pressure mechanical cell homogenizer. 1-Octanol was added to 0.1% (v/v) and the homogenate was held overnight at 4° C.

The homogenate was made 25% sucrose by addition of a 63% w/v sucrose solution. The insoluble protein fraction (refractile bodies) was separated from cell debris by continuous flow disk stack centrifugation (Westphalia SB7) at 9000 xg, 1 liter/minute and 4°–6° C. The wet pellet was mixed 50:50 (w/v) with deionized water.

Twenty-five grams of refractile body suspension (approximately 390 mg of protein) were solubilized in 250 ml of 8M urea containing 25 mM Tris, 10 mM sodium phosphate buffer (pH 8.4), 1 mM ethylenediamine tetraacetic acid (EDTA), and 4 mM dithiothreitol (DTT). After two hours at room temperature, the solution was clarified by centrifugation at 15,000×g for 15 minutes. A 150-ml aliquot of the solubilized CSF-1 was then loaded onto a 5×8 cm DEAE-Sepharose (Pharmacia) column equilibrated in 6M urea containing 25 mM Tris, 10 mM sodium phosphate buffer (pH 7.0). The column was washed with 1 bed volume of the above solution, which had been modified to contain 1M DTT and 1 mM EDTA, and the CSF-1 was then eluted with a 1.4 liter salt gradient of 0–0.6M sodium chloride in the wash buffer. The CSF-1 peak eluted at approximately 0.06M sodium chloride.

The remaining 90 ml of solubilized refractile bodies was then purified over the DEAE-Sepharose column in identical fashion. The combined CSF-1 pools (165 ml) contained approximately 250 mg of protein at a purity of approximately 50%.

The CSF-1 was then refolded by diluting the DEAE-pool into refolding buffer containing 50 mM Tris (pH 8.5), 5M EDTA, 2 mM reduced glutathione, 1 mM oxidized glutathione, pre-cooled to 4° C. The CSF-1 was allowed to refold for 30 hours at 4° C. The pH of the refolded CSF-1 was then adjusted to 6.8 using 8.5% phosphoric acid solution. The solution was then clarified by centrifugation for 10 minutes at 15,000×g and loaded onto a 5×4 cm DEAE Sepharose column pre-equilibrated in 10 mM sodium phosphate, 25 mM Tris (pH 6.8). The column was washed with 300 ml of this buffer and then eluted with a 700 ml, 0–0.6M sodium chloride gradient in the same buffer system. The CSF-1 eluted at approximately 120 mM sodium chloride. Ammonium sulfate (4M stock, pH 7.0) was then added to the 95-ml DEAE pool to a final concentration of 1M. The CSF-1 was then filtered through a Nalgene 0.45 micron filter and loaded (at 4° C.) onto a 21.5×150 mm Bio-Rad TSK Phenyl-5-PW column equilibrated in depyrogenated 1.5M ammonium sulfate, 0.1M sodium phosphate (pH 7.0). The column was washed with two bed volumes of this loading buffer and then eluted in 0.1M sodium phosphate (pH 7.0) using a 45-minute gradient in which the ammonium sulfate concentration decreased from 1.5M to 0M and the ethylene glycol concentration increased from 0–60% (v/v). All operations were carried out at 4° C. under essentially pyrogen-free conditions. The CSF-1 eluted at approximately 0.6M ammonium sulfate in 30% ethylene glycol. The CSF-1 was then extensively dialyzed into 10 mM Hepes buffer (pH 7.5) containing 150 mM sodium chloride and subsequently was filter sterilized through a Millex 0.45 micron filter.

Approximately 50 mg of purified SCSF/N∇3C∇158 CSF-1 was obtained. Greater than 90% of the final CSF-1 product migrated as a single species on SDS-PAGE, and the same product was approximately 96% one species as analyzed by RP-HPLC in acetonitrile/TFA. The specific activity was about $1.5-1.7 \times 10^8$ units/mg (units determined as colony forming units equivalents using a CSF-1-dependent cell line, and protein concentration determined using $A_{280}$ nm and an extinction coefficient of 0.6, estimated from amino acid composition determinations). This specific activity is at least equivalent to, if not greater than, that of purified native Mia PaCa CSF-1. The endotoxin content of the refolded, purified CSF-1 product, determined by LAL assay, was 0.5–1 ng/mg of CSF-1.

In a similar manner, *E. coli* protein produced under control of the PL promoter from DNA encoding SCSF/N∇2C∇150 as described in copending U.S. application Ser. No. 039,657 filed Apr. 16, 1987 was refolded and purified in a similar manner. The vector used to transform the *E. coli* was prepared by substituting the appropriate synthetic fragment for the excised HindIII/BstXI DNA of the appropriate CSF-17 vector to encode the CSF/N∇2, lacking N-terminal glu-glu.

C. Conjugation of PEG*-7000 to CSF-1

The CSF-1 protein (SCSF/N∇2C∇150) in Section B was dialyzed (1 mg protein/ml) into a medium of 10 mM Hepes buffer, pH 7.2 containing 100 mM NaCl. The PEG*-7000 was dissolved rapidly in a small volume of water and immediately added to the protein solution, which was continuously stirred throughout the reaction. A 3-fold to 30-fold molar excess of PEG*-7000 over CSF-1 dimer was employed. Reaction was complete in about 30 minutes at 20° C. and in about three hours at 4° C.

The samples were analyzed by size exclusion HPLC. FIG. 3A shows the chromatogram of underivatized rCSF-1 (SCSF/N∇2C∇150) sample prior to the experiment. FIG. 3B shows the chromatogram of 100 μg of the same CSF-1 sample after derivatization with a 5-fold molar excess of PEG*-7000 for 30 minutes at 20° C. Radioimmunoassay, performed according to the method of Stanley, R. and Guilbert, *J. Imm. Methods,* 42:253–284 (1981), confirmed that the first three major absorbance peaks observed in FIG. 3B contained rCSF-1. See Table I.

The fractions 30, 32, 34, 36, 37, 38, 39, 41 and 42 were also analyzed for biological activity, using the mouse bone marrow assay described by Moore, R. et al., *J. Immunol.* (1983) 131:2397 and by Prystowsky, M. et al., *Am. J. Pathol.* (1984) 114:149, the disclosures of which references are incorporated herein by reference. Table I provides the results.

TABLE I

| Derivatization with PEG*-7000 Clone: SCSF/N∇2C∇150 | | | |
|---|---|---|---|
| Fraction #[a] | Bone Marrow[1] | RIA[1] | Bioactivity Ratio[2] |
| 30 | 0 | 215,000 | 0 |
| 32 | 51,900 | 288,000 | 0.18 |
| 34 | 175,100 | 576,000 | 0.30 |
| 36 | 210,700 | 454,000 | 0.46 |
| 37 | 522,000 | 886,000 | 0.59 |

TABLE I-continued

| Derivatization with PEG*-7000 Clone: SCSF/N∇2C∇150 | | | |
|---|---|---|---|
| Fraction #[a] | Bone Marrow[1] | RIA[1] | Bioactivity Ratio[2] |
| 38 | 809,300 | 445,000 | 1.82 |
| 39 | 660,000 | 348,000 | 1.90 |
| 41 | 1,281,000 | 800,000 | 1.60 |
| 42 | 1,048,000 | >1,000,000 | ND |

[a]Fractions were assayed after dilution to about 1000 RIA U/ml.
[1]Units/ml
[2]Bioactivity ratio = bioassay divided by RIA
ND = Not determined The results in Table I and those below show that the unreacted rCSF-1 and the smallest molecular weight peak of derivatized rCSF-1 retained approximately full bioactivity (within experimental error). Larger species retained much less residual bioactivity. The reaction with PEG*-7000 apparently did not significantly affect the radioimmunoassay (RIA) reactivity of CSF-1, because the unfractionated, derivatized rCSF-1 retained approximately full RIA immunoreactivity per mg of protein.

D. Conjugation of PEG″-11,000 to CSF-1

Biologically active protein was purified and refolded after expression of a construct encoding SCSF/C∇150 in *E. coli* under control of the $P_L$ promoter in a vector constructed as described in U.S. Ser. No. 039,654 filed Apr. 16, 1987, assigned to the same assignee and incorporated herein by reference. The strain used was an *E. coli* λ lysogen, DG116, transformed with the plasmid 0/E p$P_L$ CSF-17 asp59/C∇150 (ATCC No. 67,389). The protein was produced intracellularly in a monomeric, insoluble form, and purified and refolded as described in copending U.S. application Ser. No. 114,001 filed Oct. 27, 1987, the disclosure of which is incorporated herein by reference.

A total of 2 mg of this purified CSF-1 at 1 mg/ml protein was dialyzed into Hepes buffer at pH 7.2 containing 100 mM NaCl. The PEG″-11,000 was dissolved rapidly in a small volume of water and immediately added to the protein solution, which was continuously stirred throughout the reaction. An 8-fold molar excess of PEG″-11,000 over CSF-1 dimer was employed. Reaction was completed in 30 minutes at 20° C. This CSF-1 reacted with the PEG″-11,000 in a fashion very similar to the reaction of SCSF/N∇2C∇150 with the PEG*-7000. As Table II shows, mild PEGylation (1–2 per dimer) again had minimal effect upon bioactivity, while the highly modified pool had significantly reduced activity.

TABLE II

| | Comparison of Derivatization of rCSF-1 With PEG″-11,000 and PEG*-7000 | |
|---|---|---|
| Extent of PEGylation[1] | PEG*7000 % Bioactive (Compared to Underivatized SCSF/N∇2C∇150) | PEG″-11,000 % Bioactive (Compared to Underivatized SCSF/C∇150) |
| Multiple | 0–20 | 8–11 |
| 1 to 2 per CSF-1 dimer | 100 | 90–100 |

[1]Estimated from apparent native molecular weight as measured by SEC-HPLC and SDS-PAGE.

FIG. 4 shows a size exclusion HPLC chromatogram of 8 mg of rCSF-1 (SCSF/C∇150) derivatized with PEG″-11,000. The mildly derivatized fraction, pooled as shown in the figure, was found to retain essentially full biological activity, and to migrate with an apparent molecular weight of 80,000 daltons on sizing, and 45,000 daltons on nonreduced SDS-PAGE (FIG. 8). This fraction was recovered at an overall yield of about 20%.

The difference in sizes of PEG-CSF estimated by these two techniques is consistent with observations made by others. PEG can alter the ability of a protein to bind SDS, affecting mobility on SDS-PAGE; and it can also affect size exclusion estimations, e.g., by hydrophobic interaction with the column matrix.

The endotoxin level of this sample, as assayed by the Limulus amebocyte lysate (LAL) assay, was found to be less than 1 ng/absorbance unit at 280 nm ($A_{280}$ unit) protein. (LAL assay is described by a product brochure (1982) for Pyrotell brand of LAL available from Associates of Cape Cod, Inc., Woods Hole, Mass.; it is also described by Watson et al. (eds.) "Endotoxins and Their Detection with the Limulus Amebocyte Lysate Test", *Proceedings of an International Conference on Endotoxin Standards and Limulus Amebocyte Lysate Use with Parenteral Drugs.* Alan R. Liss, Inc., New York (1982); and by Levin et al. (1964) *Bull. Johns. Hopkins Hosp.*, 115:265.)

E. Conjugating of PEG*-4800 to CSF-1

The same conditions used for PEG"-11,000 were used to react the rCSF-1 from the clone SCSF/C∇150 with PEG*-4800. The CSF-1 was successfully derivatized, and the pool that was mildly derivatized (at one or two sites) retained essentially full bioactivity.

F. Pharmacokinetics of PEGylated CSF-1 and Unmodified CSF-1 in Rats

Three male CD rats (Charles River Breeding Labs, Wilmington, Mass.) of average weight 161 g were injected in the tail vein with 1 mg/kg of the mildly derivatized fraction of PEG"-11,000-derivatized CSF-1 from the SCSF/C∇150 clone described above and shown in FIG. 8. Blood plasma samples were collected by an indwelling catheter, and CSF-1 titer was determined by RIA. Urine samples were collected at 0, 30, and 120 minutes and assayed. Additional data were also collected using the underivatized rCSF-1 and rCSF-1 expressed in mammalian cells (COS) that arises from a glycosylated 522-amino acid precursor (LCSF). The rats in the experiments with unmodified CSF-1 had an average weight of 178 g and were injected with 125 µg/kg of the unmodified CSF-1. All other conditions were the same.

Figure 5:
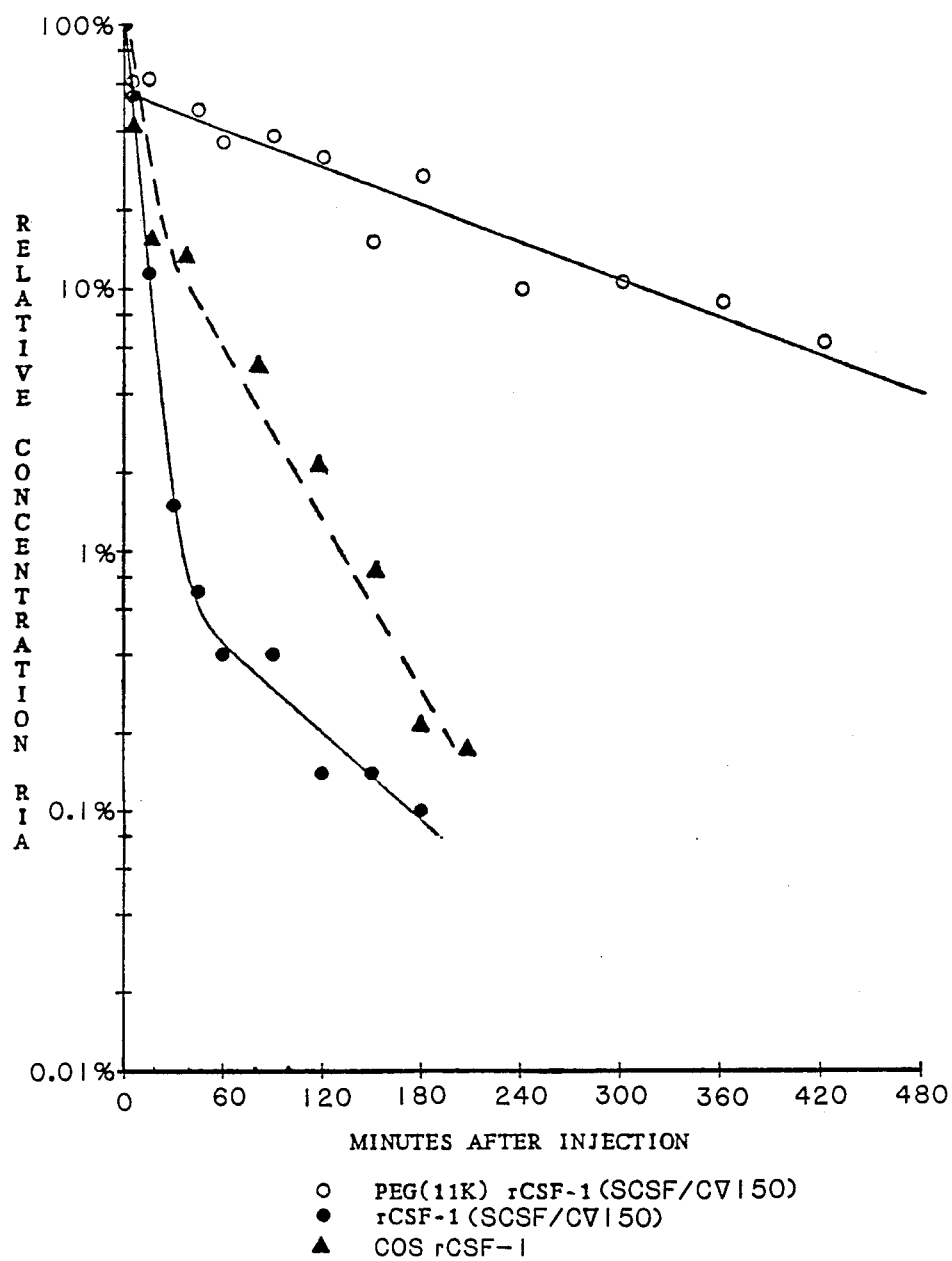
FIG. 5 shows a graph of CSF-1 concentration in rat blood plasma versus time for *E. coli* rCSF-1 (SCSF/C∇150), the dimeric product derived from the rCSF-1 with the sequence in FIG. 2 [lacking the leader sequence and a C-terminal sequence, but retaining essentially all of the N-terminal methionine present in the *E. coli* construct], rCSF-1 expressed in mammalian cells (COS) that arises from a glycosylated 522-amino acid precursor (LCSF) and PEG-11,000-derivatized *E. coli* rCSF-1 (SCSF/C∇150).

FIG. 5 compares the time courses of blood clearance of modified and unmodified CSF-1 protein. The systemic clearance is calculated by dividing the dose by the area under the blood plasma curve. The data show that the systemic clearance of derivatized rCSF-1 in the blood is 0.302 ml/min/kg versus 3.84 ml/min/kg for underivatized rCSF-1. This represents a 12.7-fold extended residence time of the derivatized as compared to the underivatized protein.

Figure 6:
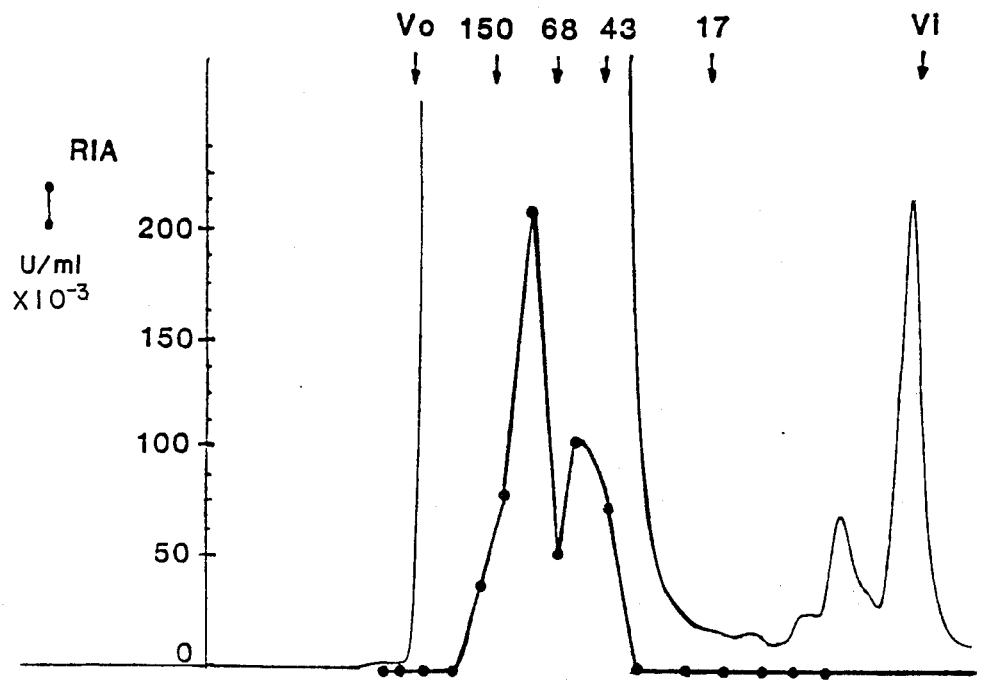
FIG. 6 shows a size exclusion HPLC chromatogram of rat blood plasma 120 minutes after intravenous injection of PEG-11,000-derivatized rCSF-1 (SCSF/C∇150). Radioimmunoassay (RIA) and absorbance at 280 nm are plotted.

FIG. 6 shows size exclusion HPLC of the rat blood plasma 120 minutes after injection of the derivatized CSF-1 (SCSF/C∇150). This figure shows that the RIA-detectable rCSF-1 signal in the blood plasma was 43–80 Kd in apparent size two hours after intravenous injection. This observation suggests that the RIA signal that was measured in the pharmacokinetic experiment (at 120 min.) represents intact PEG-rCSF-1 and rCSF-1.

Western blotting by the technique of Burnette, WN (1981) *Anal. Biochem.* 112:195–203 (developed with an recombinant CSF-1 capable of detecting CSF-1 fragments, followed by $^{125}$I-protein A) of a non-reduced SDS-PAGE gel of urine and plasma verified that the rCSF-1 antigen detected by Western blotting was apparently intact, dimeric, and the same size as the material that was injected.

EXAMPLE II

Preparation of PEGylated CSF-1 Via A Second Linkage Method

A. Preparation of PEG-Ester

1. The carboxymethyl derivative of mPEG-5000 was prepared:

Sodium-naphthalene was prepared by addition of 0.15 g Na to a solution of 0.64 g naphthalene in about 20 ml tetrahydrofuran (THF) freshly distilled from sodium benzophenone. Monomethylpoly(ethylene glycol) of average molecular weight of 5000 ("mPEG 5000") was dried overnight in a vacuum desiccator with $P_2O_5$. The Na-napthalene solution was added dropwise to a solution of 2.5 g mPEG 5000 in 50 ml dry THF (freshly distilled). When the green color persisted in the solution to indicate excess, base addition was ceased and 1.2 ml $BrCH_2COOCH_3$ was added dropwise. The green disappeared and the mixture became cloudy. The mixture was stirred overnight at room temperature. The cloudy mixture was poured into a flask containing about 70 ml cold ether. The precipitate was collected by vacuum filtration and washed with ether. The dry solid was dissolved in 75 ml 1M NaOH and stirred at room temperature for 2.5 hours to hydrolyze the methyl ester. The pH was adjusted to about 3 by addition of HCl and the solution concentrated on a rotary evaporator. The residue was taken up in $CH_2Cl_2$ and stirred for about one hour. Insoluble material was filtered off and the solution was poured into ether. The solid was collected by vacuum filtration, washed with ether, and dried in a vacuum desiccator over $P_2O_5$. This yielded the desired carboxymethyl mPEG-5000 acid. The acid was titrated to demonstrate that complete conversion had taken place. The preparation of carboxymethyl mPEG-5000 was repeated at a larger scale. The precipitate was collected and dried. Yield 8.5 g. Titration showed about 102% acid. The reference for this experiment is A. F. Buckmann et al., *Makromol. Chem.* 182:1379 (1981).

2. Para-nitrophenyl ester of carboxymethyl mPEG-5000 was prepared:

A total of 1 g mPEG-5000 acid ($2 \times 10^{-4}$ moles) was dissolved in 3 ml $CHCl_3$. To this solution was added 0.28 g p-nitrophenol ($2 \times 10^{-4}$ moles). The solution became pale yellow. Then 0.041 g of dicyclohexyl carbodiimide (DCC) ($2 \times 10^{31\ 4}$ moles) was dissolved in a small amount of $CHCl_3$ and added dropwise to the PEG-acid solution at room temperature. After about 10 minutes of stirring, 2 µl of the $CHCl_3$ mixture was added to 1.0 ml 0.01M phosphate buffer, pH 7.0. The absorbance at 400 nm of the p-nitrophenol anion was 0.2443. 5N NaOH was added, increasing the $A_{400}$ to 0.5847 (% ester is 58.2% as calculated by the formula below:

$$\% \text{ ester} = \frac{A_{400} \text{ after NaOH} - A_{400} \text{ before NaOH}}{A_{400} \text{ after NaOH}} \times 100$$

After about three hours of reaction 1 μl of the CHCl₃ mixture was added to 1.0 ml of 0.01M phosphate, pH 7.0. The $A_{400}$ was 0.2238. When 50 μl 5N NaOH was added, the $A_{400}$ was 1.154, yielding 80.6% ester.

A precipitate, dicyclohexylurea, appeared and was filtered off through a glass fiber filter and washed with CHCl₃. The ester was precipitated by adding about 300 ml anhydrous ethyl ether. The mixture was allowed to precipitate for about three hours and was then filtered through a glass frit. The precipitate was then redissolved in CHCl₃, reprecipitated with about 100 ml ethyl ether, and filtered through a medium glass frit. A small amount of damp solid was dissolved in 0.01M phosphate buffer, pH 7.0. The $A_{400}$ was 0.0240; when 50 μl 5N NaOH was added, the $A_{400}$ increased to 3.330 (% ester was 99.3).

The main precipitate was dried in a vacuum desiccator overnight. The flask in which it was contained was washed with water and the residues were lyophilized. A total of 4 mg of the precipitate was then dissolved in 2 ml 0.01M phosphate at pH 7.0 ($A_{400}$=0.0276). When 50 μl 5N NaOH was added, the $A_{400}$ was 3.50 (offscale). A total of 200 μl of the solution was diluted to 800μ 0.01M phosphate, pH 7.0. The $A_{400}$ was 0.7985. Calculated % ester=99.3.

A total of 1.5 m9 of lyophilized residues was dissolved in 1.0 ml of 0.01M phosphate, pH 7.0. The absorbance was 0.0680. A total of 50 μl of 5N NaOH was added and the $A_{400}$ was 1.106 (% ester - 93.9). The residues on the filter from the main precipitate were washed with water and lyophilized over a weekend. The weight was 131 mg of fluffy white powder. A small amount was dissolved in 0.01M phosphate, pH 7, and the $A_{400}$ was 0.0859. On adding 50 μl 5N NaOH, the $A_{400}$ was 0.6794 (87.4% ester).

Structure of ester:

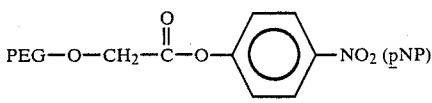

B. PEGylation of CSF-1 (asp₅₉SCSF/C▽150)

The para-nitrophenyl ester just described was coupled with the asp₅₉SCSF/C▽150 refolded protein described in Example I as follows:

The rCSF-1 (200 μg at 1 mg/ml) was dialyzed into 20 mM Hepes buffer, pH 7.2, containing 100 mM NaCl. A total of 0.8 mg of the para-nitrophenyl ester was dissolved in a small volume of water and 259 μg of this solution was immediately added to the SCSF/C▽150. The conjugation was carried out at 20° C. for four hours, and the samples were analyzed by size exclusion HPLC. The mildly derivatized rCSF-1 (corresponding to about 1 or 2 PEG molecules per CSF-1) retained essentially full bioactivity as assayed on mouse bone marrow.

If the reaction is carried out in cuvettes in a dual-beam Hewlett-Packard spectrophotometer, release of para-nitrophenol anion can be monitored, permitting the coupling reaction to be stopped reproducibly after a given amount of release has occurred.

EXAMPLE III

A. Preparation of PEGylated CSF-1 (SCSF/N▽3C▽158)

An E. coli strain HW22, transformed with the plasmid pJN653 containing the SCSF/N▽3C▽158 gene (deposited with the American Type Culture Collection on Nov. 12, 1987) was grown in a 10-liter fermenter in basal medium containing 96 mM (NH₄)₂SO₄, 28 mM KH₂PO₄, 4 mM Na₃ citrate.2H₂O, 1.7 ml/l TK9 (30 mM ZnSO₄, 30 mM MgSO₄, 1 mM CuSO₄) with sterile additions of 6.5 g/l glucose, 2.2 mM MgSO₄.7H₂O, 95 μM FeSO₄.7H₂O, and 26 mg/l thiamine.HCl. The cells were grown at 30° C. to an absorbance at 680 nm of 10, and casamino acids were then added to 2%. CSF-1 expression was induced by shifting the temperature of the culture to 37° C. After four hours the absorbance at 680 nm reached 79. The cells were then harvested by five-fold concentration and diafiltered against 10 volumes of 5 mM EDTA, pH 8.5, using Dorr-Oliver tangential cross-flow microporous filtration. The cells were disrupted by three passes at 7,500 psi (22.5 mPa) in a Manton-Gaulin high pressure mechanical cell homogenizer. 1-Octanol was added to 0.1% (v/v) and the homogenate held overnight at 4° C.

The homogenate was made 25% sucrose by addition of a 63% w/v sucrose solution. The insoluble protein fraction (refractile bodies) was separated from cell debris by continuous flow disk stack centrifugation (Westphalia SB7) at 9000 ×g, 1 liter/minute and at 4°-6° C. The wet pellet was mixed 50:50 (w/v) with deionized water and stored at −20° C. in aliquots.

The refractile body suspension was then solubilized, refolded, and purified as described in Example 1. The final specific activity was about $1.5 \times 10^8$ units/mg in a CSF-1 bioassay performed on a CSF-1 dependent cell line.

At a concentration of 2.6 mg/ml in 10 mM Hepes buffer, pH 7.5 and 100 mM NaCl, 40 mg of the refolded CSF-1 above was incubated with stirring at 20° C. PEG"-11,000 was dissolved in 200 μl of fold molar excess of PEG"-11,000 over CSF-1 dimer (the PEG"-11,000 was approximately 55% non-hydrolyzed and active). After 30 minutes of incubation, the reaction was stopped by addition of 2 moles of caminocaproate per mole of PEG"-11,000, from a 1M stock solution. The sample was concentrated to 6 ml by Amicon Centricon-30 centrifugation and purified by size exclusion HPLC in three identical 2-ml-load runs. The column used was DuPont Biosil TSK 250, 600 m, equilibrated in 0.2M Na₂HPO₄/NaH₂PO₄ buffer pH 7.0.

The $A_{280}$ peaks of mildly PEGylated protein in the three runs were pooled (pool 1, SEC) and concentrated to a final 2-ml volume, which was reinjected on the same column. The active, PEGylated fractions were pooled and concentrated.

The final pool (pool 2, SEC), representing 15% of the starting material, consisted of 6 mg of CSF-1 that had approximately 100% of the initial bioactivity of the unmodified CSF-1 and contained a major species of PEG-CSF-1 that migrated at about 45 K apparent Mr on SDS-PAGE. Small amounts (about 10%) of unmodified CSF-1 and more highly modified CSF-1 remained in the pooled product. Characterization of size exclusion chromatography (SEC) pools 1 and 2 is shown in the tables below:

| Sample | $A_{280}$ Units | Yield (%) | Endotoxin (LAL as described above) (ng/mg protein) |
|---|---|---|---|
| Unmodified rCSF-1 | 40.0 | 100 | 0.14 |
| Pool 1, SEC | 12.2 | 30 | ND* |
| Pool 2, SEC | 6.2 | 15 | 0.43 |

*Not done

| Sample | RIA (as described above) ("units"/ $A_{280}$ unit) | Bioassay (using a CSF-1 dependent cell line)(units/ $A_{280}$ unit) | Bioassay (using a CSF-1 dependent cell line)(units/ mg) |
|---|---|---|---|
| Unmodified rCSF-1 | $1 \times 10^8$ | $1 \times 10^8$ | $1.5 \times 10^8$ |
| Pool 2, SEC | $2.7 \times 10^8$ | $1.1 \times 10^8$ | $1.6 \times 10^8$ |

B. Pharmacokinetics of PEGylated CSF-1 (SCSF/N∇3C∇158)

The same conditions as described in Example I were used to estimate the average intravenous clearance rate in three rats of CSF-1 and PEG-CSF-1 described in Section A of this example, except that the doses for both PEGylated and non-PEGylated CSF-1 were 6 mg/kg.

Figure 7:
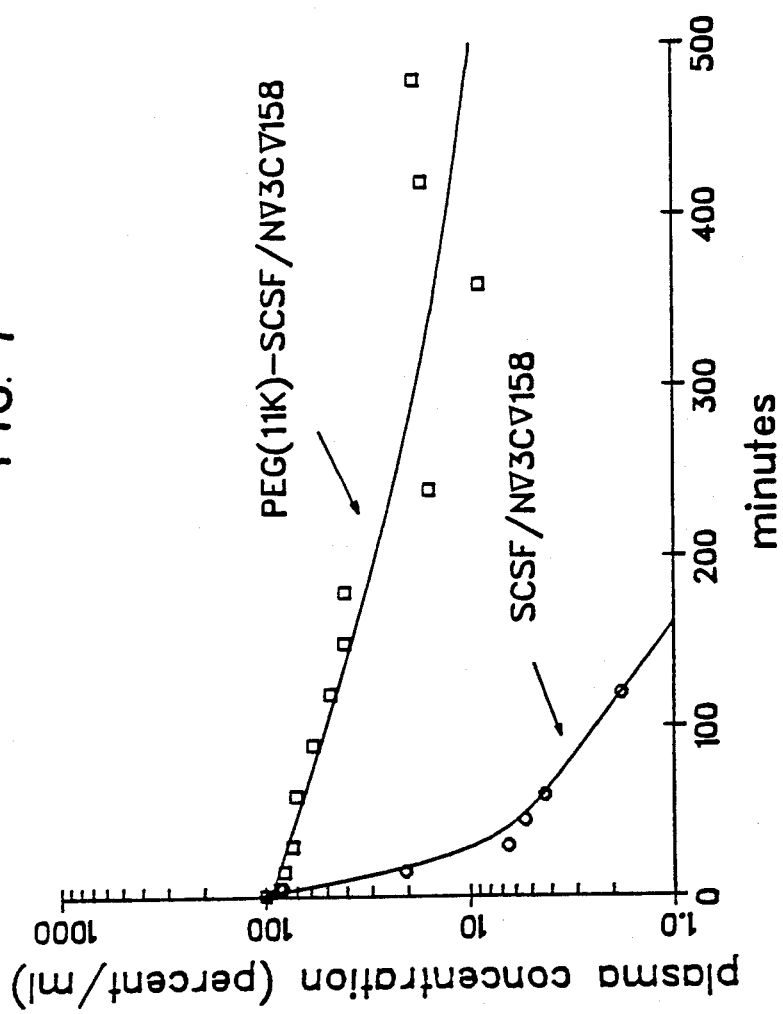
FIG. 7 shows a graph of CSF-1 concentration in rat blood plasma versus time for *E. coli* rCSF-1 (SCSF/N∇3C∇158) and for the same protein derivatized with 11,000 PEG.

FIG. 7 shows the curve of relative concentration of CSF-1 from the blood of three rats versus time after intravenous injection. The clearance was found to be about 0.63 ml/min/kg for PEGylated CSF-1 and 7.50 ml/min/kg for non-PEGylated CSF-1 (three hours as opposed to five minutes). This represents about a 12-fold increase in average residence time in the blood for the PEGylated molecule.

EXAMPLE IV

In vivo Efficacy of PEGylated CSF-1 (SCSF/N∇3C∇158): bacterial infection model

Groups of five mice were injected intraperitoneally (ip) on day −1 (a day prior to infection with a lethal dose of E. coli SM18) with the SCSF/N∇3C∇158 described in Example III, PEGylated SCSF/N∇3C∇158 prepared as described in Example III, or saline (control group). Two CSF-1 dosage groups (10 μg/mouse and 50 μg/mouse) were used. At day 0, all mice were injected ip with a lethal dose ($5 \times 10^7$ cells) of E. coli SM18. The number of mice surviving was followed for five days. The results are shown in the table below:

| | Number of Mice Surviving after day: | | | | | |
|---|---|---|---|---|---|---|
| | 1 | 2 | 3 | 4 | 5 | 6 |
| Control (saline injected) | 2 | 0 | 0 | 0 | 0 | 0 |
| Unmodified CSF-1 | | | | | | |
| 10 μg | 3 | 2 | 2 | 2 | 2 | 2 |
| 50 μg | 3 | 3 | 3 | 3 | 3 | 3 |
| PEGylated CSF-1 | | | | | | |
| 10 μg | 2 | 2 | 1 | 1 | 1 | 1 |
| 50 μg | 5 | 4 | 3 | 3 | 3 | 3 |

The results show that there is a dose-dependent effect of rCSF-1 on survival. The slight difference between the modified and unmodified CSF-1 in efficacy in this single experiment is not statistically significant. PEGylation did not reduce the efficacy detected by this protocol.

Other Embodiments

The reaction herein may also be carried out employing polyvinyl alcohol or a polyoxyethylated polyol. An active POG-CSF-1 may be prepared as follows.

Polyoxyethylated glycerol (POG) of molecular weight 5000 may be obtained from Polysciences. To 10 g of POG may be added 2.28 g glutaric anhydride (a 10-fold excess over POG). The mixture may be stirred for two hours at 110° C. and cooled. This may be dissolved in 20 ml $CHCl_3$ and poured slowly into 500 ml ether with vigorous stirring. The product may be collected and rinsed with ether to yield about 90% POG-glutarate product. This product may be reacted with N-hydroxysuccinimide as described in Example IA to yield the active ester POG-glutaryl N-hydroxysuccinimide (POG*). Then one of the CSF-1 proteins described above may be reacted with the POG*.

Nitrile-substituted polyvinyl alcohol may also be used to prepare an activated polyvinyl alcohol for conjugation to the CSF-1.

Deposits

The following cultures described more fully in copending U.S. application Ser. Nos. 876,819 filed June 20, 1986, 039,654 filed Apr. 16, 1987, and 039,657 filed Apr. 16, 1987, were deposited in the Cetus Master Culture Collection (CMCC), 1400 Fifty-Third Street, Emeryville, Calif. 94608 U.S.A. and in the American Type Culture Collection (ATCC), 12301 Parklawn Drive, Rockville, Md. 20852 U.S.A. The CMCC and ATCC accession numbers and ATCC deposit dates for the deposited samples are:

| Culture Designation | CMCC No. | ATCC No. | ATCC Deposit Date |
|---|---|---|---|
| Phage pH CSF-1 in E. coli DG98 | | 40,177 | April 2, 1985 |
| pHCSF-1 λ Charon 4A | 2312 | 40,185 | May 21, 1985 |
| CSF-17 in E. coli MM294 | 2347 | 53,149 | June 14, 1985 |
| PCSF-asp59 | 2705 | 67,139 | June 19, 1985 |
| pCSF-gln52 | 2708 | 67,140 | June 19, 1986 |
| pCSF-pro52 | 2709 | 67,141 | June 19, 1985 |
| pCSF-Bam | 2710 | 67,142 | June 19, 1986 |
| pCSF-BamBC1 | 2712 | 67,144 | June 19, 1986 |
| pCSF-Gly150 | 2762 | 67,145 | June 19, 1986 |
| pcDBCSF4 (or pcDBhuCSF-4) | 2894 | 67,250 | October 24, 1986 |
| pPhoA-LCSF/C∇221 in MM294 | 3084 | 67,391 | April 14, 1987 |
| O/E pP$_L$LCSF/N∇3C∇221 in DG116 | 3095 | 67,390 | April 14, 1987 |
| O/E pP$_L$CSF-17 asp59/C∇150 | 3044 | 67,389 | April 14, 1987 |

| Culture Designation | CMCC No. | ATCC No. | ATCC Deposit Date |
|---|---|---|---|
| in DG116 | | | |
| pP$_L$CSF-17 asp$_{59}$/C▽150 in DG116 | 2946 | 67,383 | April 7, 1987 |
| pJN653 (SCSF/N▽3C▽158) in HW22 | 3204 | 67,561 | November 12, 1987 |

The deposits above were made pursuant to a contract between the ATCC and the assignee of this patent application, Cetus Corporation. The contract with ATCC provides for permanent availability of the progeny of these plasmids and the cell line to the public on the issuance of the U.S. patent describing and identifying the deposit or the publications or upon the laying open to the public of any U.S. or foreign patent application, whichever comes first, and for availability of the progeny of these plasmids and the cell line to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the plasmids and the cell line on deposit should die or be lost or destroyed when cultivated under suitable conditions, they will be promptly replaced on notification with a viable culture of the same plasmids and cell line.

In summary, the present invention is seen to provide various recombinant CSF-1 molecules selectively derivatized with water-soluble polymers of different sizes using different chemical linkers. Derivatization of the CSF-1 increases the apparent molecular weight of the CSF-1 and increases its in vivo half-life in the plasma of rats. The derivatization may also increase the solubility of the CSF-1 in aqueous medium at physiological pH and may decrease its immunogenicity by decreasing or eliminating aggregation or by shielding its antigenic determinants.

The foregoing written specification is considered to be sufficient to enable one skilled in the art to practice the invention. The present invention is not to be limited in scope by the cultures deposited, since the deposited embodiments are intended as a single illustration of one aspect of the invention, and any cultures that are functionally equivalent are within the scope of this invention. The deposit of materials herein does not constitute an admission that the written description herein contained is inadequate to enable the practice of any aspect of the invention, including the best mode thereof, nor are they to be construed as limiting the scope of the claims to the specific illustrations that they represent. Indeed, various modifications of the above-described modes for carrying out the invention that are obvious to those skilled in the field of pharmaceutical formulation or related fields are intended to be within the scope of the following claims.

What is claimed is:

1. A biologically active composition comprising a protein that stimulates the formation of primarily macrophage colonies in the in vitro colony stimulating factor-1 (CSF-1) assay, which protein is covalently conjugated to a water-soluble polymer selected from the group consisting of polyethylene or polypropylene glycol homopolymers, polyoxyethylated polyols, and polyvinyl alcohol, wherein said homopolymer is unsubstituted or substituted at one end with an alkyl group.

2. The composition of claim 1 wherein the protein is a native human CSF-1.

3. The composition of claim 1 wherein the protein is a recombinant human CSF-1.

4. The composition of claim 3 wherein the protein is recombinantly expressed in bacteria and is a homodimer with predicted amino acid sequence selected from the group consisting of LCSF/C▽150 through C▽464; tyr$_{59}$LCSF/C▽150 through C▽464; SCSF/C▽150 through C▽166; asp$_{59}$SCSF/C▽150 through C▽166 and the gln$_{52}$ muteins and N▽2 and N▽3 muteins thereof, wherein LCSF is coded for by the sequence shown as amino acids 1–522 of FIG. 2 and SCSF is coded for by the sequence shown as amino acids 1–224 of FIG. 1.

5. The composition of claim 4 wherein the protein is a homodimer with predicted amino acid sequence selected from the group consisting of LCSF/C▽150; tyr59LCSF/C▽150; LCSF/C▽190; tyr$_{59}$LCSF/C▽190; LCSF/C▽191; tyr$_{59}$LCSF/C▽191; LCSF/C▽221; tyr$_{59}$LCSF/C▽221; LCSF/C▽223; tyr$_{59}$LCSF/C▽223; LCSF/C▽236; tyr$_{59}$LCSF/C▽236; LCSF/C▽238; tyr$_{59}$LCSF/C▽238; LCSF/C▽249; tyr$_{59}$LCSF/C▽249; LCSF/C▽258; tyr$_{59}$LCSF/C▽258; LCSF/C▽411; tyr$_{59}$LCSF/C▽411; LCSF/C▽464; tyr$_{59}$LCSF/C▽464; SCSF/C▽150; SCSF/C▽153; SCSF/C▽158; and the corresponding asp$_{59}$SCSFs; the gln$_{52}$ muteins and N▽2 and N▽3 muteins thereof.

6. The composition of claim 5 wherein the protein is a homodimer coded for by a sequence selected from the group consisting of LCSF/C▽150, LCSF/C▽190, LCSF/C▽221, tyr59LCSF/C▽150, tyr$_{59}$LCSF/C▽190, tyr$_{59}$LCSF/C▽221, SCSF/C▽158, SCSF/C▽150, and the N▽2 and N▽3 muteins thereof.

7. The composition of claim 6 wherein the protein is a homodimer coded for by a sequence selected from the group consisting of SCSF/C▽150, SCSF/N▽2C▽150, and SCSF/N▽3C▽158.

8. The composition of claim 1 wherein the protein is a recombinant heterodimer consisting of one subunit containing a cysteine residue with a free sulfhydryl group reactive with the polymer.

9. The composition of claim 1 wherein the protein is a murine CSF-1.

10. The composition of claim 1 wherein the protein is a human CSF-1 expressed in and secreted from a eukaryotic host.

11. The composition of claim 10 wherein the protein is a dimer coded for by a sequence selected from the group consisting of LCSF/C▽150; tyr$_{59}$LCSF/C▽150; LCSF/C▽190; tyr$_{59}$LCSF/C▽190; LCSF/C▽191; tyr$_{59}$LCSF/C▽191; LCSF/C▽221; tyr$_{59}$LCSF/C▽221; LCSF/C▽223;

tyr$_{59}$LCSF/C∇223; LCSF/C∇236; tyr$_{59}$LCSF/C∇236; LCSF/C∇238; tyr$_{59}$LCSF/C∇238; LCSF/C∇249; tyr$_{59}$LCSF/C∇249; LCSF/C∇258; tyr$_{59}$LCSF/C∇258; LCSF/C∇411; tyr$_{59}$LCSF/C∇411; LCSF/C∇464; tyr$_{59}$LCSF/C∇464; SCSF/C∇150; SCSF/C∇153; SCSF/C∇158; and the gln$_{52}$ muteins thereof.

12. The composition of claim 1 wherein said polymer has an average molecular weight of about 1000 to 100,000 daltons.

13. The composition of claim 1 wherein said polymer has an average molecular weight of 4000 to 40,000 daltons.

14. The composition of claim 1 wherein said polymer is conjugated to the protein via reaction with the active ester of a carboxylic acid of said polymer.

15. The composition of claim 14 wherein said polymer is an unsubstituted polyethylene glycol homopolymer, a monomethyl polyethylene glycol homopolymer or a polyoxyethylated glycerol.

16. The composition of claim 1 wherein the protein is conjugated via one or two free amino groups thereof, and the polymer contains an N-hydroxysuccinimide ester, p-nitrophenyl ester or 4-hydroxy-3-nitrobenzene sulfonic acid ester group that reacts with the free amino groups of the protein.

17. The composition of claim 16 wherein the amino group(s) conjugated is (are) in lysine residue(s) or the N-terminal amino acid or a combination thereof.

18. The composition of claim 1 wherein the protein is conjugated via one or more cysteine residue(s) and the polymer contains a maleimido or haloacetyl group that reacts with the free sulfhydryl group of the cysteine residue.

19. The composition of claim 1 wherein the protein is glycosylated and is conjugated to the polymer via at least one of the carbohydrate moieties on the protein, and the polymer contains an amino, hydrazine, or hydrazide group that reacts with free aldehydes formed by oxidation of the carbohydrate moieties.

20. The composition of claim 19 wherein the protein is a dimeric product of a recombinant CSF-1 clone recombinantly expressed in a eukaryotic host.

21. The composition of claim 20 wherein the eukaryotic host is mammalian, insect, yeast, or fungal cells.

22. A pharmaceutical preparation comprising the composition of claim 1 dissolved in a pharmaceutically acceptable aqueous carrier medium.

23. The preparation of claim 22 wherein the protein is refolded, and purified in vitro and is the product of a recombinant CSF-1 clone recombinantly expressed in bacteria.

24. The preparation of claim 23 wherein the protein is a biologically active, refolded CSF-1 dimer having an endotoxin content of less than 1.0 ng/mg of CSF-1 and substantially free of pyrogens.

25. A method of prophylactic or therapeutic treatment of infectious diseases in mammals comprising administering to said mammal an immunotherapeutically effective amount of the preparation of claim 22.

26. A method for treating tumor burden in mammals comprising administering to said mammal an immunotherapeutically effective amount of the preparation of claim 22.

* * * * *